US009429584B2

(12) United States Patent
Matsumura et al.

(10) Patent No.: US 9,429,584 B2

(45) Date of Patent: Aug. 30, 2016

(54) ANTIBODY AGAINST INSOLUBLE FIBRIN

(71) Applicant: National Cancer Center, Chuo-ku, Tokyo (JP)

(72) Inventors: Yasuhiro Matsumura, Kashiwa (JP); Masahiro Yasunaga, Kashiwa (JP); Yohei Hisata, Kashiwa (JP)

(73) Assignee: NATIONAL CANCER CENTER, Tokyo (JP)

( * ) Notice: Subject to any disclaimer, the term of this patent is extended or adjusted under 35 U.S.C. 154(b) by 0 days.

(21) Appl. No.: 14/770,864

(22) PCT Filed: Feb. 27, 2014

(86) PCT No.: PCT/JP2014/054925

§ 371 (c)(1),
(2) Date: Aug. 27, 2015

(87) PCT Pub. No.: WO2014/133093

PCT Pub. Date: Sep. 4, 2014

(65) Prior Publication Data

US 2016/0011217 A1 Jan. 14, 2016

(30) Foreign Application Priority Data

Feb. 28, 2013 (JP) ................................ 2013-039625

(51) Int. Cl.

| | |
|---|---|
| ***G01N 33/86*** | (2006.01) |
| ***C07K 16/18*** | (2006.01) |
| ***A61K 47/48*** | (2006.01) |
| ***C07K 16/36*** | (2006.01) |

(52) U.S. Cl.

CPC .......... *G01N 33/86* (2013.01); *A61K 47/48538* (2013.01); *C07K 16/18* (2013.01); *C07K 16/36* (2013.01); *C07K 2317/33* (2013.01); *C07K 2317/34* (2013.01); *G01N 2333/75* (2013.01); *G01N 2800/226* (2013.01)

(58) Field of Classification Search

None

See application file for complete search history.

(56) References Cited

U.S. PATENT DOCUMENTS

| | | | |
|---|---|---|---|
| 4,916,070 | A | 4/1990 | Matsueda et al. |
| 2003/0124056 | A1 | 7/2003 | Carr et al. |
| 2008/0009077 | A1 | 1/2008 | Matsuo et al. |

FOREIGN PATENT DOCUMENTS

| | | | |
|---|---|---|---|
| JP | 8-301900 | A | 11/1996 |
| JP | 9-104700 | A | 4/1997 |
| JP | 9-127108 | A | 5/1997 |
| JP | 2001-354700 | A | 12/2001 |
| JP | 2008-29353 | A | 2/2008 |
| JP | 2009-149686 | A | 7/2009 |
| JP | 2012-72 | A | 1/2012 |

OTHER PUBLICATIONS

Editor by Merz et al Chapter 14 authors by Ngo et al. (1995) "The Protein Folding Problem and Tertiary Structure Prediction," Computational Complexity Protein Structure Prediction, and the Levinthal Paradox pp. 492-495.*

Wells (1990) Biochemistry 29: 8509-8517.*

Bork (2000) Genome Research 10:398-400.*

Skolnick (2000) Trends in Biotech. 18: 34-39.*

Smith et al. (1997) Nature Biotechnology 1999 15: 1222-1223).*

An International Preliminary Report on Patentability mailed Sep. 11, 2015, which issued during the prosecution of Applicant's PCT/JP2014/054925.

An International Search Report mailed Apr. 22, 2014, which issued during the prosecution of Applicant's PCT/JP2014/054925.

Paul D. Stein et al., "Incidence of Venous Thromboembolism in Patients Hospitalized with Cancer", The American Journal of Medicine vol. 119, pp. 60-68, (2006).

Masahiro Yasunaga et al., "New concept of cytotoxic immunoconjugate therapy targeting cancer-induced fibrin clots", Cancer Science, vol. 102, No. 7, pp. 1396-1402, Jul. 2011.

Yohei Hisada et al., "Discovery of an uncovered region in fibrin clots and its clinical significance", Scientific Reports, vol. 3, Article No. 2604. (7 pages total). Sep. 2013.

* cited by examiner

*Primary Examiner* — Jacob Cheu

(74) *Attorney, Agent, or Firm* — Sughrue Mion, PLLC

(57) ABSTRACT

With the intention of providing an antibody which does not bind to fibrinogen and which has a high affinity for and a high specificity to insoluble fibrin, it is found that a site comprising the amino acids at positions 231 to 246 of the fibrinogen Bβ chain and a site comprising the amino acids at positions 232 to 246 of the fibrinogen γ chain are bound to each other in a fibrinogen molecule. Further, it is shown that when fibrinogen is converted to insoluble fibrin, the binding is released, and these sites are exposed. It is also found that antibodies obtained by immunization with these sites do not bind to fibrinogen and have high affinity for and high specificity to insoluble fibrin.

12 Claims, 10 Drawing Sheets

Fig. 14

```
mkrmvswsfh klktmkhlll lllcvflvks qgvndneegf fsarghrpld kkreeapslr
papppisggg yrarpakaaa tqkkverkap daggclhadp dlgvlcptgc qlqeallqqe
rpirnsvdel nnnveavsqt ssssfqymyl lkdlwqkrqk qvkdnenvvn eysselekkg
lyidetvnsn iptnlrvlrs ilenlrskiq klesdvsaqm eycrtpctvs cnipvvsgke
ceelirkgge tsemyliqpd ssvkpyrvyc dmntenggwt viqnrqdgsv dfgrkwdpyk
qgfgnvatnt dgknycglpg eywlgndkis qltrmgptel liemedwkgd kvkahyggft
vqneankyqi svnkyrgtag nalmdgasql mgenrtmtih ngmffstydr dndgwltsdp
rkqcskedgg gwwynrchaa npngryywgg qytwdmakhg tddgvvwmnw kgswysmrkm
smkirpffpq q
```

Fig. 15

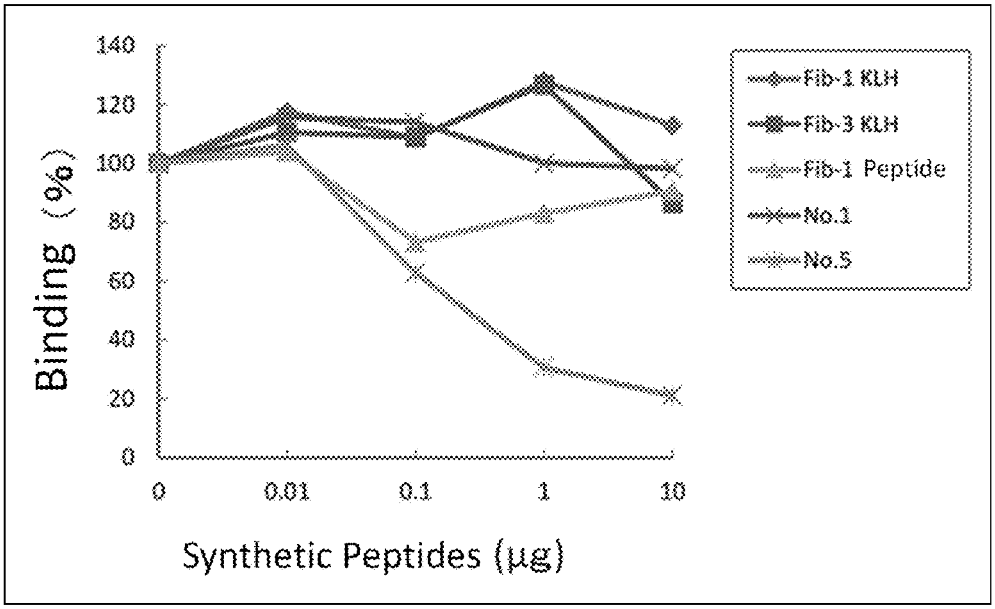

Fig. 18

[ L Chain Variable Region of Fib-0355 Antibody ]

L-CDR1 L-CDR2

PSSLAVSAGEKVTMSCKSS [QSVLYSSNQK] NYLAWYQQKPGQSPKLLI [YWASTRES]

L-CDR3

GVPDRFTGSGSGTDFTLTISSVQAEDLAVYYCQQ [YLSS] YTFGG

[ H Chain Variable Region of Fib-0355 Antibody]

H-CDR1 H-CDR2

GPELKKPGETVKISCKASG [YTFTNYG] MNWVKQAPGKGLKWMGWI [NTNTGE]

H-CDR3

PTYAEEFKGRFAFSLETSASTAYLQINNLKNEDTATYFCA [RLLDY] WGQGTTLTVSS

Fig. 19

[ L Chain Variable Region of 34-105 Antibody]

L-CDR1 L-CDR2

DIVITQSPASLAVSLGQRATISYRAS [KSVSTSGYSY] MHWNQQKPGQPPRLLIY [LVS]

L-CDR3

NLESGVPARFSGSGSGTDFTLNIHPVEEEDAATYYC [QHIRELTR] SEGGPSWK

[ H Chain Variable Region of 34-105 Antibody]

H-CDR1 H-CDR2

EVKLQESGGGLVKPGGSLKLSCAAS [GFTFSSYA] MSWVRQTPEKRLEWVAA [ISSGGTT]

H-CDR3

YYPDSVKGRFTISRDNARNILYLQMSSLRSEDTAMYYC [VRGGTIGAY] WGQGTLVTVSA

ANTIBODY AGAINST INSOLUBLE FIBRIN

CROSS REFERENCE TO RELATED APPLICATIONS

This application is a National Stage of International Application No. PCT/JP2014/054925 filed Feb. 27, 2014, claiming priority based on Japanese Patent Application No. 2013-039625 filed Feb. 28, 2013, the contents of all of which are incorporated herein by reference in their entirety.

TECHNICAL FIELD

The present invention relates to an antibody which binds to insoluble fibrin and which does not bind to fibrinogen, and a reagent and method for detecting insoluble fibrin, the reagent comprising the antibody. The present invention also relates to a reagent and method for diagnosing a thrombus-related disease using the antibody. Moreover, the present invention relates to a conjugate comprising the antibody and an antitumor part.

BACKGROUND ART

It has been revealed that when a blood vessel is injured, and the blood is in contact with the injured vascular wall or the subcutaneous tissue in the blood vessel or the tissue factor flows into the blood, the blood coagulation reaction is started in which fibrinogen in the blood is converted to insoluble fibrin, and a net of the fibrin functions as a strong haemostatic plug and hardens the wound.

It has been suggested from the past that blood coagulation is closely related to cancer (described in "Edema Caused by Thrombi in Limbs of Patient with Gastric Cancer" by a French surgeon Trousseau in the 1800s). Recent clinical epidemiologic data have revealed that the incidence of thrombosis due to hypercoagulation is significantly higher inpatients with most types of cancer including pancreatic cancer, gastric cancer, and brain tumors than in healthy people (NPL 1). It is thought that insoluble fibrin accumulation, coagulation necrosis, and angiogenesis due to abnormal coagulation occur repeatedly in cancer tissues with the progression of the cancer.

Insoluble fibrin is not present in tissues under normal physiological conditions in contrast to its precursor, fibrinogen, which is widely found in a living body. Fibrinogen is cleaved by thrombin which has leaked out from the blood vessel and which has been activated, and forms fibrin monomers. Then, the fibrin monomers are polymerized and cross-linked to form fibrin fiber. In this manner, insoluble fibrin is formed. For this reason, the insoluble fibrin is present specifically in tissues under a pathological condition such as hemorrhage or inflammation, and is formed at the occurrence of a pathological condition involving coagulation, such as cancer, myocardial infarction, or cerebral infarction. Accordingly, insoluble fibrin is a marker molecule of such thrombus-related diseases, and it can be truly said that insoluble fibrin present in a cancer tissue is a cancer-specific molecule especially under a situation where any cerebral or cardiovascular disease such as myocardial infarction or cerebral infarction is not present. As described above, insoluble fibrin is shown to be related with the thrombus formation and important diseases, and hence there is a demand for development of means for specifically detecting fibrin.

In view of such a situation, antibodies have been developed as means for detecting fibrin (PTLs 1 to 6). In addition, the present inventors have also developed an antibody which binds to fibrin and which does not bind to fibrinogen, and clarified the usefulness of the antibody (PTL 7).

However, since insoluble fibrin is formed when terminal portions are cleaved from the precursor, fibrinogen, the amino acid sequences of insoluble fibrin and fibrinogen are completely the same except for the presence or absence of the parts removed by the cleavage. Moreover, soluble fibrin (FDPs, fibrin degradation products) formed by degradation of insoluble fibrin with plasmin or the like may be present in a living organism in some cases. Accordingly, detection of insoluble fibrin in the presence of molecules (fibrinogen, FDPs, and the like) having extremely high homologies in terms of the amino acid sequence and the structure requires an antibody having a higher affinity for and a higher specificity to insoluble fibrin.

CITATION LIST

Patent Literature

[PTL 1] Japanese Patent Application Publication No. 2001-354700

[PTL 2] Japanese Patent Application Publication No. 2009-149686

[PTL 3] Japanese Patent Application Publication No. 2008-29353

[PTL 4] Japanese Patent Application Publication No. Hei 9-127108

[PTL 5] Japanese Patent Application Publication No. Hei 9-104700

[PTL 6] Japanese Patent Application Publication No. Hei 8-301900

[PTL 7] Japanese Patent Application Publication No. 2012-72

Non Patent Literature

[NPL 1] PD Stein et al., "Incidence of venous thromboembolism in patients hospitalized with cancer", American J Med., 2006, Vol. 119, pp. 60 to 68

SUMMARY OF INVENTION

Technical Problem

The present invention has been made in view of the above-described problems of the conventional technologies, and an object of the present invention is to provide an antibody which does not bind to fibrinogen and which has a high affinity for and a high specificity to insoluble fibrin.

Solution to Problem

To solve the above-described problems, the present inventors have intensively studied the properties and functions of the antibody (102-10 antibody) which binds to fibrin and which does not bind to fibrinogen described in PTL 7. Consequently, it has been found that the 102-10 antibody enables in vitro and in vivo detection of a thrombus formed because of cancer, cerebral infarction, myocardial infarction, an inflammatory disease, or the like. In addition, it has also been found that the 102-10 antibody does not bind to fibrinogen, but can bind to the Bβ chain among the three polypeptide chains (Aα chain, Bβ chain, and γ chain) constituting fibrinogen. Moreover, it has also been found that the epitope of the 102-10 antibody is a site comprising the amino acids at positions 231 to 246 in the fibrinogen Bβ chain.

Fibrinogen is converted to a fibrin monomer, for example, when the amino terminus of the fibrinogen Bβ chain constituting the fibrinogen is cleaved, and the fibrinogen β chain is formed. Further, the monomer is polymerized or cross-linked to form insoluble fibrin. Results of a computer simulation analysis conducted by the present inventors have revealed that the epitope in fibrinogen is a site which is present in the fibrinogen Bβ chain and which binds to the fibrinogen γ chain. Based on the results, the present inventors have assumed that the 102-10 antibody cannot bind to fibrinogen, because the epitope of the antibody is hidden in the molecule. In addition, the present inventors have assumed that the 102-10 antibody can bind to insoluble fibrin, because when the fibrin monomer is polymerized and cross-linked, the epitope in the fibrinogen β chain or the fibrinogen Bβ chain is exposed in the fibrin monomer.

On the basis of such an assumption, monoclonal antibodies were again prepared by immunization of mice using, as an antigen, each of the site comprising the amino acids at positions 231 to 246 of the fibrinogen Bβ chain and the site which binds to this site in the fibrinogen molecule and which comprises the amino acids at positions 232 to 246 of the fibrinogen γ chain. Then, the affinities of the obtained antibodies for fibrinogen and insoluble fibrin were evaluated. Each of the antibodies did not bind to fibrinogen and exhibited a high affinity for insoluble fibrin. Moreover, it has been found that each of the antibodies has a far higher affinity for insoluble fibrin than the 102-10 antibody. In addition, the amino acid sequences of the light chain and heavy chain variable regions and the complementarity determining regions of each of the currently prepared antibodies capable of binding to the site comprising the amino acids at positions 231 to 246 of the fibrinogen Bβ chain and the currently prepared antibodies capable of binding to the site comprising the amino acids at positions 232 to 246 of the fibrinogen γ chain were determined. The present invention has been made based on the above-described findings. Specifically, the present invention provides the following <1> to <11>.

<1> An antibody which binds to insoluble fibrin and which does not bind to fibrinogen, wherein the antibody binds to a site shown in SEQ ID NO: 1 or a site shown in SEQ ID NO: 2.

<2> The antibody according to <1>, comprising:

a light chain variable region comprising the amino acid sequences shown in SEQ ID NOs: 4 to 6 or amino acid sequences of SEQ ID NOs: 4 to 6 in at least one of which one or more amino acids are substituted, deleted, added, and/or inserted; and a heavy chain variable region comprising the amino acid sequences shown in SEQ ID NOs: 8 to 10 or amino acid sequences of SEQ ID NOs: 8 to 10 in at least one of which one or more amino acids are substituted, deleted, added, and/or inserted.

<3> The antibody according to <1>, comprising:

a light chain variable region comprising the amino acid sequences shown in SEQ ID NOs: 12 to 14 or amino acid sequences of SEQ ID NOs: 12 to 14 in at least one of which one or more amino acids are substituted, deleted, added, and/or inserted; and a heavy chain variable region comprising the amino acid sequences shown in SEQ ID NOs: 16 to 18 or amino acid sequences of SEQ ID NOs: 16 to 18 in at least one of which one or more amino acids are substituted, deleted, added, and/or inserted.

<4> The antibody according to <1>, comprising:

a light chain variable region comprising the amino acid sequence shown in SEQ ID NO: 3 or an amino acid sequence of SEQ ID NO: 3 in which one or more amino acids are substituted, deleted, added, and/or inserted; and a heavy chain variable region comprising the amino acid sequence shown in SEQ ID NO: 7 or an amino acid sequence of SEQ ID NO: 7 in which one or more amino acids are substituted, deleted, added, and/or inserted.

<5> The antibody according to <1>, comprising:

a light chain variable region comprising the amino acid sequence shown in SEQ ID NO: 11 or an amino acid sequence of SEQ ID NO: 11 in which one or more amino acids are substituted, deleted, added, and/or inserted; and a heavy chain variable region comprising the amino acid sequence shown in SEQ ID NO: 15 or an amino acid sequence of SEQ ID NO: 15 in which one or more amino acids are substituted, deleted, added, and/or inserted.

<6> A reagent for immunological measurement, comprising the antibody according to any one of <1> to <5>.

<7> A reagent for diagnosing a thrombus-related disease, comprising the antibody according to any one of <1> to <5>.

<8> An agent for visualizing a thrombus, comprising the antibody according to any one of <1> to <5>.

<9> A method for detecting insoluble fibrin in a sample, comprising the steps of:

(a) bringing the antibody according to any one of <1> to <5> into contact with the sample; and (b) detecting whether or not the antibody is bound to insoluble fibrin in the sample.

<10> A method for diagnosing a thrombus-related disease in a subject, comprising the steps of:

(a) bringing the antibody according to any one of <1> to <5> into contact with a sample obtained from the subject, and (b) detecting whether or not the antibody is bound to insoluble fibrin in the sample.

<11> A conjugate, comprising:

the antibody according to any one of <1> to <5>; and an antitumor part.

Advantageous Effects of Invention

According to the present invention, it is possible to provide an antibody which does not bind to fibrinogen and which has a high affinity for and a high specificity to insoluble fibrin. The use of such an antibody enables high-sensitive, reliable, and simple detection of the presence of insoluble fibrin and a thrombus and, in turn, enables diagnosis of a thrombus-related disease. In addition, the use of such an antibody enables a suitable compound or molecule to be delivered to a site where a thrombus is present, for example, to a tumor.

BRIEF DESCRIPTION OF DRAWINGS

FIG. 14 is a diagram showing the amino acid sequence of the fibrinogen Bβ chain (SEQ ID NO: 19). The amino acid sequence marked in the diagram is the region (86 amino acids) ranging from the histidine at position 179 to the lysine at position 264 of the fibrinogen Bβ chain in which the presence of the epitope of the 102-10 antibody is suggested by an amino acid sequencing analysis.

FIG. 15 is a graph showing the results of a competitive binding inhibition experiment with the 102-10 antibody using synthetic peptides comprising partial sequences of the region composed of the 86 amino acids.

FIG. 18 is a diagram showing the amino acid sequences of the light chain (L chain) variable region (SEQ ID NO: 11), the heavy chain (H chain) variable region (SEQ ID NO: 15), and the CDRs 1 to 3 thereof in an anti-β chain antibody (Fib-0355 antibody).

FIG. 19 is a diagram showing the amino acid sequences of the light chain (L chain) variable region (SEQ ID NO: 3), the heavy chain (H chain) variable region (SEQ ID NO: 7, and the CDRs 1 to 3 thereof in an anti-γ chain antibody (34-105 antibody).

DESCRIPTION OF EMBODIMENTS

<Antibody Against Insoluble Fibrin>

Figure 1:
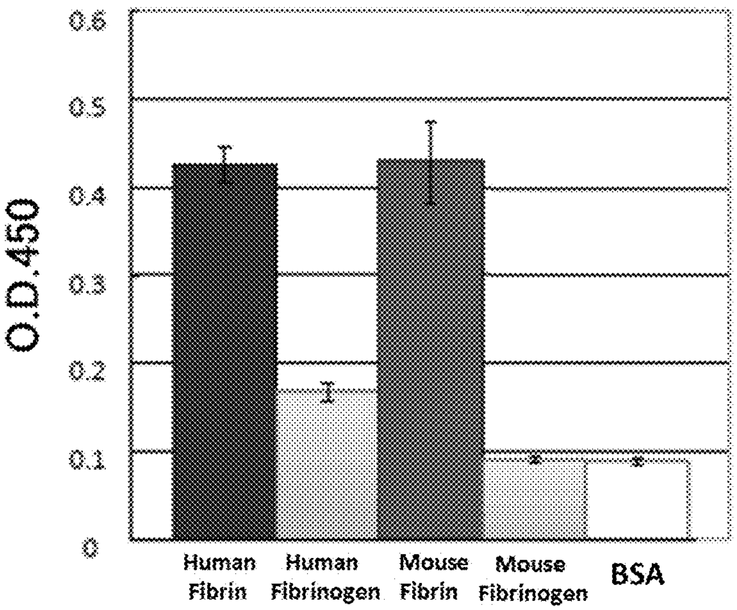
FIG. 1 is a graph showing the results obtained by analyzing the affinities of an antibody (the 102-10 antibody described in Japanese Patent Application Publication No. 2012-72) which binds to fibrin and which does not bind to fibrinogen for insoluble fibrins and fibrinogens from human and mouse by an ELISA method.

As shown in Examples described later, the present inventors have shown that each antibody whose epitope is the site comprising the amino acids at positions 231 to 246 of the fibrinogen Bβ chain or the site comprising the amino acids at positions 187 to 202 of the fibrinogen β chain (both are the site shown in SEQ ID NO: 1) or the site comprising the amino acids at positions 232 to 246 of the fibrinogen γ chain (the site shown in SEQ ID NO: 2) can bind to insoluble fibrin but cannot bind to fibrinogen.

Accordingly, the present invention provides an antibody which binds to insoluble fibrin and which does not bind to fibrinogen, wherein the antibody binds to the site shown in SEQ ID NO: 1 or the site shown in SEQ ID NO: 2.

In the present invention, the "insoluble fibrin" means one produced when a fibrin monomer is produced from fibrinogen by the action of thrombin, and the fibrin monomer is polymerized to form a hardly soluble fibrin polymer, and the fibrin polymer is cross-linked by factor XIII. Meanwhile, the "insoluble fibrin" in the present invention includes the fibrin polymer and fibrin monomers constituting the insoluble fibrin, but does not include solubilized materials produced by degradation of insoluble fibrin by plasmin or the like (FDPs, fibrin degradation products).

In the present invention, the "fibrinogen" means a complex in which two fibrinogen Aα chains, two fibrinogen Bβ chains, and two fibrinogen γ chains are bridged. When the "fibrinogen Bβ chain" is originated from human, the "fibrinogen Bβ chain" is typically a protein comprising the amino acid sequence shown in SEQ ID NO: 19. When the "fibrinogen γ chain" is originated from human, the "fibrinogen γ chain" is typically a protein comprising the amino acid sequence shown in SEQ ID NO: 20. Meanwhile, the "fibrinogen β chain" in the present invention means a protein produced when the fibrinogen Bβ chain is cleaved by the action of thrombin, and fibrinopeptide B, which is the N-terminus part of the fibrinogen Bβ chain, is removed. When the "fibrinogen β chain" is originated from human, the "fibrinogen β chain" is typically a protein comprising the amino acid sequence at positions 45 to 491 shown in SEQ ID NO: 19.

The amino acid sequence shown in SEQ ID NO: 1 is the amino acid sequence at positions 231 to 246 of the human fibrinogen Bβ chain or the amino acid sequence at positions 187 to 202 of the human fibrinogen β chain. The amino acid sequence shown in SEQ ID NO: 2 is the amino acid sequence at positions 232 to 246 of the human fibrinogen γ chain.

An "antibody" in the present invention includes all classes and subclasses of immunoglobulins. The meaning of "antibody" includes a polyclonal antibody and a monoclonal antibody, and also includes the form of a functional fragment of an antibody. A "polyclonal antibody" is an antibody preparation containing different antibodies against different epitopes. Meanwhile, a "monoclonal antibody" means an antibody (including an antibody fragment) obtained from a substantially uniform antibody population. In contrast to a polyclonal antibody, a monoclonal antibody recognizes a single determinant on an antigen. The antibody of the present invention is preferably a monoclonal antibody. The antibody of the present invention is an antibody separated and/or recovered (i.e., isolated) from components in a natural environment.

In the present invention, whether an antibody binds to insoluble fibrin and whether the antibody does not bind to fibrinogen can be determined by a method known in the technical field. Such a known method is, for example, an ELISA method using a plate coated with insoluble fibrin or fibrinogen, as shown in Examples described later.

In addition, in the present invention, an antibody having a high specificity to insoluble fibrin means an antibody which binds to fibrin with a higher affinity than affinities for other peptides and proteins. Here, a high affinity means such a high affinity that insoluble fibrin can be detected while distinguishing insoluble fibrin from other peptides and proteins by a method known in the technical field.

In addition, the antibody of the present invention can bind to insoluble fibrins from human and mouse, but does not bind to fibrinogens from human and mouse, as shown in Examples described later. Accordingly, test data obtained by using the antibody in a mouse can be extrapolated to human.

In addition, preferred modes of the monoclonal antibody of the present invention include a monoclonal antibody (Fib-0355 antibody) produced by hybridoma Fib-0355, a monoclonal antibody (Fib-3435 antibody) produced by hybridoma Fib-3435, a monoclonal antibody (13-30 antibody) produced by hybridoma 13-30, and a monoclonal antibody (34-105 antibody) produced by hybridoma 34-105, which are shown in Examples described later.

Meanwhile, other preferred modes of the monoclonal antibody of the present invention include antibodies comprising a light chain variable region comprising the light chain CDR1 to CDR3 and a heavy chain variable region comprising the heavy chain CDR1 to CDR3 of one of the above-described monoclonal antibodies produce by the hybridomas, and amino acid sequence variants thereof.

Such preferred monoclonal antibodies of the present invention include an antibody comprising:

a light chain variable region comprising the amino acid sequences of light chain CDR1 to CDR3 (the amino acid sequences shown in SEQ ID NOs: 4 to 6) or amino acid sequences of the light chain CDR1 to CDR3 in at least one of which one or more amino acids are substituted, deleted, added, and/or inserted, and a heavy chain variable region comprising the amino acid sequences of heavy chain CDR1 to CDR3 (the amino acid sequences shown in SEQ ID NOs: 8 to 10) or amino acid sequences of the heavy chain CDR1 to CDR3 in at least one of which one or more amino acids are substituted, deleted, added, and/or inserted, and an antibody comprising:

a light chain variable region comprising the amino acid sequences of light chain CDR1 to CDR3 (the amino acid sequences shown in SEQ ID NOs: 12 to 14) or amino acid sequences of the light chain CDR1 to CDR3 in at least one of which one or more amino acids are substituted, deleted, added, and/or inserted; and a heavy chain variable region comprising the amino acid sequences of heavy chain CDR1 to CDR3 (the amino acid sequences shown in SEQ ID NOs: 16 to 18) or amino acid sequences of the heavy chain CDR1 to CDR3 in at least one of which one or more amino acids are substituted, deleted, added, and/or inserted.

More preferred monoclonal antibodies of the present invention include an antibody comprising:

a light chain variable region comprising the amino acid sequence shown in SEQ ID NO: 3 or an amino acid sequence of SEQ ID NO: 3 in which one or more amino acids are substituted, deleted, added, and/or inserted; and a heavy chain variable region comprising the amino acid sequence shown in SEQ ID NO: 7 or an amino acid sequence of SEQ ID NO: 7 in which one or more amino acids are substituted, deleted, added, and/or inserted, and an antibody comprising:

a light chain variable region comprising the amino acid sequence shown in SEQ ID NO: 11 or an amino acid sequence of SEQ ID NO: 11 in which one or more amino acids are substituted, deleted, added, and/or inserted, and a heavy chain variable region comprising the amino acid sequence shown in SEQ ID NO: 15 or an amino acid sequence of SEQ ID NO: 15 in which one or more amino acids are substituted, deleted, added, and/or inserted.

Moreover, other preferred modes of the antibody of the present invention are the antibodies each of which exhibited an affinity for insoluble fibrin (an absorbance at a wavelength of 492 nm) of 0.5 or higher (more preferably 1.0 or higher, further preferably 1.5 or higher, and particularly preferably 2.0 or higher) in the ELISA shown in Example 2 described later.

Furthermore, other preferred modes of the antibody of the present invention are antibodies each of which exhibited an affinity for insoluble fibrin (an absorbance at a wavelength of 492 nm) which was 5 times or more (more preferably 10 times or more) higher than that of the 102-10 antibody described in PTL 7, in the ELISA shown in Example 2 described later.

Moreover, other preferred modes of the antibody of the present invention are the antibodies each of which had such a ratio of the affinity for insoluble fibrin to the affinity for fibrinogen (the absorbance at 492 nm) that the affinity for insoluble fibrin is 10 times or higher (more preferably 20 times or higher) than the affinity for fibrinogen in the ELISA shown in Example 2 described later.

The antibody of the present invention includes a mouse antibody, a chimeric antibody, a humanized antibody, a human antibody, and functional fragments of these antibodies. In a case where the antibody of the present invention is administered as a drug to a human, the antibody is desirably a chimeric antibody, a humanized antibody, or a human antibody from the viewpoint of side effect reduction.

In the present invention, a "chimeric antibody" is an antibody in which a variable region of an antibody of one species is linked to a constant region of an antibody of another species. A chimeric antibody can be obtained, for example, as follows. Specifically, a mouse is immunized with an antigen. A portion corresponding to an antibody variable portion (variable region) which binds to the antigen is cut out from a gene of a monoclonal antibody of the mouse, and this portion is linked to a gene of a constant portion (constant region) of an antibody derived from human bone marrow. This is incorporated into an expression vector, which is then introduced into a host for the production of a chimeric antibody. (For example, Japanese Patent Application Publication No. Hei 8-280387, U.S. Pat. No. 4,816,397, U.S. Pat. No. 4,816,567, and U.S. Pat. No. 5,807,715) Meanwhile, in the present invention, a "humanized antibody" is an antibody obtained by grafting (CDR grafting) a gene sequence of an antigen-binding site (CDR) of a non-human derived antibody onto a human antibody gene. The methods for preparing a humanized antibody are known (see, for example, EP239400, EP125023, WO90/07861, and WO96/02576). In the present invention, a "human antibody" is an antibody all regions of which are derived from human. In preparing a human antibody, it is possible to employ a screening method for production of an active antibody by human B cells, a phage display method, the use of a transgenic animal (for example, a mouse) which becomes capable of producing a repertoire of human antibodies when immunized, and the like. Methods for preparing a human antibody are known (for example, Nature, 362: 255-258 (1993), Intern. Rev. Immunol, 13: 65-93 (1995), J. Mol. Biol, 222: 581-597 (1991), Nature Genetics, 15: 146-156 (1997), Proc. Natl. Acad. Sci. USA, 97: 722-727 (2000), Japanese Patent Application Publication No. Hei 10-146194, Japanese Patent Application Publication No. Hei 10-155492, Japanese Patent No. 2938569, Japanese Patent Application Publication No. Hei 11-206387, International Application Japanese-Phase Publication No. Hei 8-509612, and International Application Japanese-Phase Publication No. Hei 11-505107).

In the present invention, a "functional fragment" of an antibody means apart (partial fragment) of an antibody which binds to the site shown in SEQ ID NO: 1 or the site shown in SEQ ID NO: 2. Specific examples thereof include Fab, Fab', F(ab')2, a variable region fragment (Fv), a disulfide-stabilized Fv, a single-chain Fv (scFv), an sc(Fv)2, a diabody, a polyspecific antibody, polymers thereof, and the like.

Here, "Fab" means a monovalent antigen-binding fragment of an immunoglobulin, composed of one light chain and a part of a heavy chain. Fab can be obtained by papain digestion of an antibody or a recombinant method. "Fab'" is different from Fab in that a small number of residues, including one or more cysteine residues in the hinge region of the antibody, are added to the carboxy terminus of a heavy chain CH1 domain. "F(ab')2" means a divalent antigen-binding fragment of an immunoglobulin, composed of two light chains and parts of two heavy chains.

A "variable region fragment (Fv)" is a smallest antibody fragment having complete antigen reorganization and binding sites. An Fv is a dimer in which a heavy chain variable region and a light chain variable region are strongly linked by non-covalent bonding. A "single-chain Fv (scFv)" includes a heavy chain variable region and a light chain variable region of an antibody, and these regions exist in a single polypeptide chain. An "sc(Fv)2" is a single chain obtained by linking two heavy chain variable regions and two light chain variable regions with a linker or the like. A "diabody" is a small antibody fragment having two antigen-binding sites. This fragment has a heavy chain variable region linked to a light chain variable region in a single polypeptide chain, and each region forms a pair with a complementary region of another chain. A "polyspecific antibody" is a monoclonal antibody having binding specificities to at least two different antigens. For example, a polyspecific antibody can be prepared by coexpression of two immunoglobulin heavy chain/light chain pairs of which the two heavy chains have different specificities.

The antibody of the present invention includes antibodies whose amino acid sequences are modified without reducing desirable activities (affinity for an antigen, specificity to an antigen, and/or other biological properties). An amino acid sequence variant of the antibody of the present invention can be prepared by introduction of a mutation into a DNA encoding the antibody chain of the present invention, or by peptide synthesis. Examples of such a modification include substitution, deletion, addition, and/or insertion of residues in the amino acid sequence of the antibody of the present invention. A site where the amino acid sequence of the antibody is modified may be in a constant region of a heavy chain or a light chain of the antibody, or in a variable region (framework region or CDR) thereof, as long as the modified antibody has activities equivalent to those of the unmodified antibody. It is conceivable that a modification on amino acids other than those in CDR has a relatively small influence on the binding affinity for an antigen. Now, screening methods for an antibody whose affinity for an antigen is enhanced by modifying amino acids in CDR are known (PNAS, 102: 8466-8471 (2005), Protein Engineering, Design & Selection, 21: 485-493 (2008), International Publication No. WO2002/051870, J. Biol. Chem., 280: 24880-24887 (2005), and Protein Engineering, Design & Selection, 21: 345-351 (2008)).

The number of amino acids modified is preferably 10 amino acids or less, more preferably 5 amino acids or less, and most preferably 3 amino acids or less (for example, 2 amino acid or less or 1 amino acid). The modification of amino acids is preferably conservative substitution. In the present invention, the term "conservative substitution" means substitution with a different amino acid residue having a chemically similar side chain. Groups of amino acid residues having chemically similar amino acid side chains are well known in the technical field to which the present invention pertains. For example, amino acids can be grouped into acidic amino acids (aspartic acid and glutamic acid), basic amino acids (lysine, arginine, histidine), and neutral amino acids such as amino acids having a hydrocarbon chain (glycine, alanine, valine, leucine, isoleucine, and proline), amino acids having a hydroxy group (serine and threonine), sulfur-containing amino acids (cysteine and methionine), amino acids having an amide group (asparagine and glutamine), an amino acid having an imino group (proline), and amino acids having an aromatic group (phenylalanine, tyrosine, and tryptophan).

Moreover, the term "having equivalent activities" means that the affinity for an antigen is equivalent to (for example, 70% or higher of, preferably 80% or higher of, and more preferably 90% or higher of) those of a reference antibody (typically, the Fib-0355 antibody, the Fib-3435 antibody, the 13-30 antibody, or the 34-105 antibody shown in Examples described later). The affinity for an antigen can be evaluated by an ELISA method as described above.

In addition, in the present invention, for the purpose of increasing the stability of the antibody or other purposes, an amino acid which undergoes deamidation or an amino acid next to an amino acid which undergoes deamidation may be substituted with a different amino acid to suppress the deamidation. In addition, the stability of the antibody can also be increased by substituting glutamic acid with a different amino acid. The present invention also provides an antibody thus stabilized.

If the antibody of the present invention is a polyclonal antibody, the polyclonal antibody can be obtained as follows. Specifically, a host animal is immunized with a polypeptide comprising an amino acid sequence of an antigen (SEQ ID NO: 1 or SEQ ID NO: 2), a partial peptide thereof, cells expressing any of these, or the like). Then, an antiserum from the animal is purified by conventional means (for example, salting-out, centrifugation, dialysis, column chromatography, or the like). Thus, the polyclonal antibody can be obtained. Meanwhile, a monoclonal antibody can be prepared by a hybridoma method or a recombinant DNA method.

The hybridoma method is typically a method by Kohler and Milstein (Kohler& Milstein, Nature, 256: 495 (1975)). Antibody-producing cells used in the cell fusion process in this method are spleen cells, lymph node cells, peripheral blood leucocytes, or the like of an animal (for example, mouse, rat, hamster, rabbit, monkey, or goat) immunized with the antigen. It is also possible to use antibody-producing cells obtained by treating the above-described cells, lymphocytes, or the like isolated in advance from a non-immunized animal with the antigen in a culture medium. As myeloma cells, various known cell lines can be used. The antibody-producing cells and the myeloma cells may be ones originated from different animal species, as long as they can be fused. However, the antibody-producing cells and the myeloma cells are preferably originated from the same animal species. Hybridomas can be produced, for example, by cell fusion between mouse myeloma cells and spleen cells obtained from a mouse immunized with the antigen. By the subsequent screening, a hybridoma which produces a monoclonal antibody specific to the site shown in SEQ ID NO: 1 or 2 can be obtained. The monoclonal antibody specific to the site shown in SEQ ID NO: 1 or 2 can be obtained by culturing the hybridoma, or from the ascitic fluid of a mammal to which the hybridoma is administered.

The recombinant DNA method is a method by which the antibody of the present invention is produced as a recombinant antibody as follows. A DNA encoding the antibody of the present invention is cloned from a hybridoma, a B cell, or the like. The cloned DNA is incorporated into a suitable vector, which is then introduced into host cells (for example, a mammalian cell line, *E. coli*, yeast cells, insect cells, plant cells, or the like) for the production of the antibody of the present invention. (For example, P. J. Delves, Antibody Production: Essential Techniques, 1997 WILEY, P. Shepherd and C. Dean Monoclonal Antibodies, 2000 OXFORD UNIVERSITY PRESS, Vandamme A. M. et al., Eur. J. Biochem. 192: 767-775 (1990)). For the expression of the DNA encoding the antibody of the present invention, DNAs encoding a heavy chain and a light chain may be incorporated separately into expression vectors to transform the host cells. Alternatively, the DNAs encoding a heavy chain and a light chain may be incorporated into a single expression vector to transform the host cells (see International Publication No. WO94/11523). The antibody of the present invention can be obtained in a substantially pure and homogeneous form by culturing the host cells, followed by separation and purification of the host cells or the culture liquid. For the separation and purification of the antibody, an ordinary method used for polypeptide purification can be employed. Once a transgenic animal (cattle, goat, sheep, pig, or the like) into which the antibody gene is incorporated is prepared by using a transgenic animal production technique, it is also possible to obtain a large amount of the monoclonal antibody derived from the antibody gene in milk of the transgenic animal.

Accordingly, the present invention makes it possible to provide a DNA encoding the antibody of the present invention, an expression vector comprising the DNA, a transformant which comprises the DNA or the expression vector and which produces the antibody of the present invention, a method for producing the antibody of the present invention, comprising the steps of: culturing the transformant; and separating and purifying an antibody in the transformant or a culture liquid thereof, and a hybridoma which produces the antibody of the present invention or which comprises an DNA encoding the antibody of the present invention.

Moreover, the present invention also makes it possible to provide a method for producing an antibody which binds to insoluble fibrin and which does not bind to fibrinogen, comprising immunization with a polypeptide comprising the amino acid sequence shown in SEQ ID NO: 1 or a polypeptide comprising the amino acid sequence shown in SEQ ID NO: 2. Moreover, it is also possible to provide an antigen comprising the amino acid sequence shown in SEQ ID NO: 1 or 2 for producing an antibody which binds to insoluble fibrin and which does not bind to fibrinogen.

<Reagent for Immunological Measurement>

As shown in Examples described later, insoluble fibrin in a sample can be detected by using the antibody of the present invention. The detection can be conducted based on any measurement method using an antibody, i.e., any immunological measurement method. For example, the insoluble fibrin can be detected by utilizing an immunohistochemical staining method and an immunoelectron microscopic method or immunoassay (enzyme immunoassay (ELISA, EIA), fluoroimmunoassay, radioimmunoassay (RIA), immunochromatography, Western blotting, or the like).

The sample to be tested is not particularly limited, and examples thereof include tissue or cell samples (tissues or cells of cancer in the stomach, duodenum, large intestine, pancreas, gallbladder, bile duct, bronchi, lung, and the like), biological fluid samples (gastric mucus, duodenal juice, pancreatic juice, bile, ascitic fluid, phlegm, bronchoalveolar lavage fluid, blood, serum, plasma, and the like), and the like. For, for example, immunostaining, a tissue sample (a biopsy specimen or a resected specimen) or a cytology sample is preferably used as the sample.

In the immunological measurement method of the present invention, insoluble fibrin is detected by allowing insoluble fibrin in a sample to bind to the antibody of the present invention, and detecting the binding. In the present invention, the term "detection" includes not only the detection of the presence or absence of insoluble fibrin, but also quantitative detection of insoluble fibrin and immunostaining of insoluble fibrin.

The immunoassay of insoluble fibrin typically includes bringing a sample to be tested into contact with the antibody of the present invention, and detecting the bound antibody by an approach known in the technical field. The term "contact" means that insoluble fibrin present in sample and the antibody of the present invention are placed in a state where they can approach and bind to each other. Examples of the contact include operations such as application of an antibody-containing solution onto a solid sample, immersion of a solid sample in an antibody-containing solution, and mixing of a liquid sample with an antibody-containing solution.

The immunoassay can be conducted in a liquid phase system or a solid phase system. Moreover, the mode of the immunoassay is not limited, and may be a direct solid phase method, as well as a sandwich method, a competitive method, or the like.

The antibody of the present invention can also be used histologically for in situ detection of insoluble fibrin as in an immunohistochemical staining method (for example, an immunostaining method) or an immunoelectron microscopic method. The in situ detection can be conducted by, for example, cutting a histological sample from a subject (a biopsy tissue sample, a paraffin-embedded tissue section, or the like), and bringing a labeled antibody into contact with the histological sample.

Regarding operations of the immunoassay, the immunoassay can be conducted by a known method (Ausubel, F. M. et al. (eds.), Short Protocols in Molecular Biology, Chapter 11 "immunology,", John Wiley & Sons, Inc. 1995). Alternatively, a conjugate of insoluble fibrin and the antibody may be separated by a known separating technique (a chromatographic method, a salting-out method, an alcohol precipitation method, an enzymatic method, a solid phase method, or the like), and the signal of the label may be detected.

When, for example, a solid-phase system is employed for the immunoassay, the antibody may be immobilized on a solid-phase support or carrier (resin plate, membrane, beads, or the like), or the sample may be immobilized. For example, the antibody is immobilized on a solid-phase support, and the support is washed with a suitable buffer, followed by treatment with a sample. Next, the solid-phase support is subjected to the second washing using the buffer to remove the unbound antibody. Then, the antibody bound onto the solid support can be detected by a conventional technique to detect the binding between insoluble fibrin in the sample and the antibody. Alternatively, after a solid sample is treated with a solution containing the antibody, and then the unbound antibody is removed by washing with a buffer, the antibody bound onto the solid sample can be detected by a conventional technique.

The binding activity of an antibody can be measured by a well-known method. Those skilled in the art can determine an effective and optimal measurement method for each assay depending on the type and mode of the immunoassay to be employed, the type of the label to be used, the object to be labeled, and the like.

In the present invention, to facilitate the detection of the reaction between the antibody of the present invention and insoluble fibrin present in the sample, the antibody of the present invention is labeled to directly detect the reaction, or a labeled secondary antibody, a biotin-avidin complex, or the like is used to indirectly detect the reaction. Examples of labels usable in the present invention and detection methods thereof are described below.

For the enzyme immunoassay, for example, peroxidase, β-galactosidase, alkaline phosphatase, glucose oxidase, acetylcholinesterase, lactate dehydrogenase, amylase, or the like can be used. An enzyme-inhibiting substance, a coenzyme, or the like can also be used. Each of the enzymes can be conjugated to the antibody by a known method using a cross-linking agent such as glutaraldehyde or a maleimide compound.

For fluoroimmunoassay, for example, fluorescein isothiocyanate (FITC), tetramethylrhodamine isothiocyanate (TRITC), or the like can be used. These fluorescent labels can be conjugated to the antibody by a conventional technique.

For radioimmunoassay, for example, tritium, iodine 125, iodine 131, or the like can be used. The radioactive label can be conjugated to the antibody by a known method such as the chloramine T method or the Bolton and Hunter method.

For example, when the antibody of the present invention is directly labeled with a label as described above, a complex of insoluble fibrin and the antibody is formed by bringing a sample into contact with the labeled antibody of the present invention. For quantification, after the unbound labeled antibody is separated, the amount of insoluble fibrin in the sample can be determined based on the amount of the bound labeled antibody or the amount of the unbound labeled antibody.

Alternatively, when, for example, a labeled secondary antibody is used, the antibody of the present invention and the sample are reacted with each other (primary reaction), and the obtained complex is further reacted with the labeled secondary antibody (secondary reaction). The primary reaction and the secondary reaction may be conducted in reverse order, or may be conducted simultaneously or after a time interval. The primary reaction and the secondary reaction result in the formation of a complex of fibrin—the antibody of the present invention—the labeled secondary antibody or a complex of the antibody of the present invention—fibrin—the labeled secondary antibody. In addition, when quantification is conducted, the unbound labeled secondary antibody is separated, and then the amount of insoluble fibrin in the sample can be determined based on the amount of the bound labeled secondary antibody or the amount of the unbound labeled secondary antibody.

When the biotin-avidin complex system is used, a biotinylated antibody and the sample are reacted, and then the obtained complex is reacted with a labeled avidin. Since avidin can specifically bind to biotin, the binding between the antibody and insoluble fibrin can be determined by detecting the signal of the label attached to avidin. The label attached to avidin is not particularly limited, and is preferably, for example, an enzyme label (peroxidase, alkaline phosphatase, or the like).

The signal of the label can also be detected by a method known in the technical field. For example, when an enzyme label is used, a substrate which is degraded by an enzymatic action to develop a color is added, the amount of the substrate degraded is optically measured to determine the enzymatic activity, and this enzymatic activity is converted to the amount of the bound antibody, and the amount of the antibody is calculated by comparison with a standard value. The substrate varies depending on the type of the enzyme used. For example, when peroxidase is used as the enzyme, 3,3',5,5'-tetramethylbenzidine (TMB), diaminobenzidine (DAB), or the like can be used. Meanwhile, when alkaline phosphatase is used as the enzyme, para-nitrophenol or the like can be used. The fluorescent label can be detected and quantified by using, for example, a fluorescence microscope, a plate reader, or the like. When the radioactive label is used, the amount of radiation emitted by the radioactive label is measured with a scintillation counter or the like.

The present invention also relates to a reagent for immunological measurement of insoluble fibrin, comprising the antibody of the present invention. In the reagent for immunological measurement of the present invention, the antibody may be labeled. In addition, the antibody may be in a free form, or may be immobilized onto a solid-phase support (for example, a membrane, beads, or the like).

In addition to the antibody of the present invention, the reagent for immunological measurement may comprise components useful for conducting an immunological measurement method. Examples of such components include a buffer, a sample treatment reagent, a label, a competitor, a secondary antibody, and the like for use in the immunoassay. The use of the reagent for immunological measurement of the present invention enables easy and simple detection of insoluble fibrin in the sample.

<Reagent for Diagnosing Thrombus-Related Disease>

Since the antibody of the present invention specifically reacts with human insoluble fibrin as shown in Examples described later, the antibody of the present invention can be used for a reagent for diagnosing a fibrin-related disease or disorder, for example, a thrombus-related disease. In the present invention, a "thrombus-related disease" means a disease or disorder whose condition is related to the presence of a thrombus. Such thrombus-related diseases include, but are not limited to, infarction, for example, myocardial infarction, cerebral infarction, cerebral hemorrhage, cerebral embolism, cerebral thrombosis, subarachnoid hemorrhage, pulmonary infarction, and the like, and cancer, for example, pancreatic cancer, gastric cancer, esophageal cancer, colorectal cancer, colon cancer, ovarian cancer, breast cancer, and pulmonary cancer. By detecting the presence of insoluble fibrin, it is possible to diagnose the presence or absence of a thrombus-related disease, diagnose the progress (aggravation or alleviation) of a thrombus-related disease, and specify the position of a thrombus-related disease.

The diagnosing reagent of the present invention comprises the above-described antibody of the present invention. Accordingly, the detection of insoluble fibrin contained in a sample taken from a subject with a thrombus-related disease (for example, infarction or cancer) or with a suspected thrombus-related disease by using the diagnosing reagent of the present invention makes it possible to rapidly and simply diagnose the presence of a thrombus-related disease in the subject, the progress of the thrombus-related disease in the subject, and the position of the thrombus-related disease in the subject. A reagent for diagnosing a disease or disorder using such an immunological measurement method is well-known, and those skilled in the art can easily select suitable components other than the antibody. In addition, the diagnosing reagent of the present invention can be used for any procedure, as long as the procedure is intended to conduct an immunological measurement method.

<Visualization/In Vivo Imaging of Thrombus, Delivery to Thrombus Site>

When administered to a subject, the antibody of the present invention binds to insoluble fibrin in the subject. Accordingly, the use of the antibody of the present invention makes it possible to visualize insoluble fibrin, i.e., a thrombus in a subject. Moreover, by conjugating a compound or molecule to the antibody of the present invention, it is possible to deliver the compound or molecule to insoluble fibrin, i.e., a thrombus site in the subject.

The agent for visualizing a thrombus of the present invention preferably comprises a labeled antibody of the present invention. As the label, any label known in the in vivo imaging field can be used. Such labels include fluorescent substances, for example, IRDye800 series, fluorescein, FITC, fluorescent metals ($^{152}Eu$, lanthanide series, and the like), and the like; chemiluminescent or bioluminescent substances, for example, luminol, imidazole, luciferin, luciferase, green fluorescent protein (GFP), and the like; radioisotopes, for example, $^{89}Zr$, $^{99}mTc$, $^{123}I$, $^{131}I$, $^{97}Ru$, $^{67}Cu$, $^{11}C$, $^{3}N$, and the like; paramagnetic isotopes, for example, $^{153}Gd$, $^{157}Gd$, $^{55}Mn$, $^{162}Dy$, $^{52}Cr$, $^{56}Fe$, and the like; and contrast agents, for example, gadolinium, gadolinium complexes, iodine contrast agents, and the like. The antibody and the label can be conjugated to each other by a method known in the technical field. For example, the antibody and the label may be chemically conjugated directly to each other. Alternatively, the antibody and the label may be indirectly conjugated to each other through a suitable linker. Examples of the linker include p-isothiocyanatobenzyl-desferrioxamine B, thiocarbamate, amide, carbamate, and maleimide.

In addition, in the present invention, by conjugating the antibody of the present invention to a compound or a molecule such as a drug or a prodrug in place of the label, the compound or molecule can be delivered to a site where insoluble fibrin is present in the subject, i.e., a thrombus site. Such drugs and prodrugs include known thrombolytic agents (for example, urokinase, streptokinase, tissue-type plasminogen activator), and the like. Thrombus-targeting agents of such drugs and prodrugs are also included in the present invention.

Moreover, the present invention provides a conjugate comprising the antibody of the present invention and an antitumor part. The antibody of the present invention binds to a thrombus site (fibrin) in a tumor as described above. Hence, by conjugating the antibody to the antitumor part, the antitumor part can be delivered to a tumor. Anti-tumor parts which can be conjugated to the antibody of the present invention are not particularly limited, as long as the antitumor parts are known in the technical field. The antitumor parts include anticancer agents, for example, alkylating agents such as irinotecan (CPT-11), irinotecan metabolite SN-38 (10-hydroxy-7-ethyl-camptothecin), adriamycin, Taxol, 5-fluorouracil, nimustine, and ranimustine, antimetabolites such as gemcitabine and hydroxycarbamide, plant alkaloids such as etoposide and vincristine, anticancer antibiotics such as mitomycin and bleomycin, platinum agents such as cisplatin; molecularly targeted agents such as sorafenib and erlotinib, methotrexate, cytosine arabinoside, 6-thioguanine, 6-mercaptopurine, cyclophosphamide, ifosfamide, busulfan, MMAE (monomethyl auristatin E), DM-1 (mertansine), calicheamicin, and the like; radioisotopes, for example, boron 10 ($^{10}B$), indium 111 ($^{111}In$), yttrium 90 ($^{90}Y$), and the like. The antitumor part preferably has such a molecular weight that, after the delivery of the conjugate of the present invention to a thrombus site in a tumor tissue, the antitumor part can be liberated from the conjugate at the site and reach the entire tumor tissue.

In addition, the antibody can be conjugated to the antitumor part by a method known in the technical field, and may be directly conjugated or indirectly conjugated. For example, a covalent bond can be utilized for the direct conjugation. Bonding through a linker can be utilized for the indirect conjugation.

In the present invention, the antibody is preferably conjugated to the antitumor part through a linker. The conjugation of the two molecules through a linker can attenuate the antigenicity of the antitumor part, which is preferable for administration to a subject. Common technologies of linkers are described in, for example, Hermanson, G. T. Bioconjugate Techniques, Academic Press, 1996; Harris, J. M. and Zalipsky, S. (eds), Poly(ethylene glycol), Chemistry and Biological Applications, ACS Symposium Series, 1997; and Veronese, F. and Harris, J. M. (eds), Peptide and protein PEGylation, Advanced Drug Delivery Review 54 (4), 2002.

A linker means a divalent or higher-valent group which links two compounds. Linkers usable in the present invention include, but are not particularly limited to, polyalkylene glycol linkers, alkylene groups, peptides, sugar chains, and other polymeric carriers. The alkylene moiety of an alkylene glycol which is a constitutional unit of a polyalkylene glycol linker has 1 to 3000 carbon atoms, preferably 2 to 1000 carbon atoms, and more preferably 2 to 100 carbon atoms. The molecular weight of the polyalkylene glycol linker is generally 30 to 50000 Da, and preferably 500 to 30000 Da. The polyalkylene glycol linker is preferably a polyethylene glycol (PEG) linker. The alkylene group may be linear or branched.

Moreover, the linkers include linear linkers (divalent linkers) and branched linkers (trivalent or higher-valent linkers). A linear linker is provided with the antitumor part at one end thereof and the antibody of the present invention at the other end. A branched linker is generally provided with the antitumor part at each branch (each chain) and the antibody at the other end.

A specific example of the linear chain linker is a linker of the following formula I:

[Chem. 1]

(I)

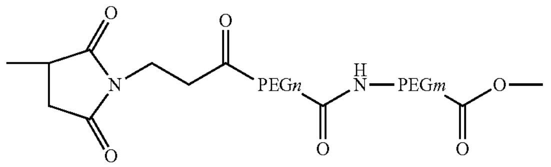

[In the formula, PEG is a polyethylene glycol chain, and each of n and m is the number of ethylene glycol units and independently represents an integer of 5 to 100].

The linker of formula I is generally linked to the antibody at the terminus having the succinimidyl group, and to the antitumor part at the other terminus.

Moreover, another specific example of the linear chain linker is a linker of formula II:

[Chem. 2]

(II)

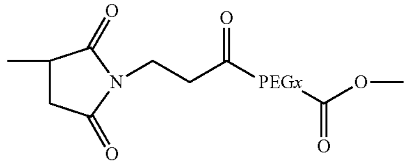

[In the formula, PEG is a polyethylene glycol chain, and x is the number of ethylene glycol units and represents an integer of 5 to 100].

The linker of formula II is generally linked to the antibody at the terminus having the succinimidyl group and to the antitumor part at the other terminus.

A specific example of the branched linker is a linker of formula III:

[Chem. 3]

(III)

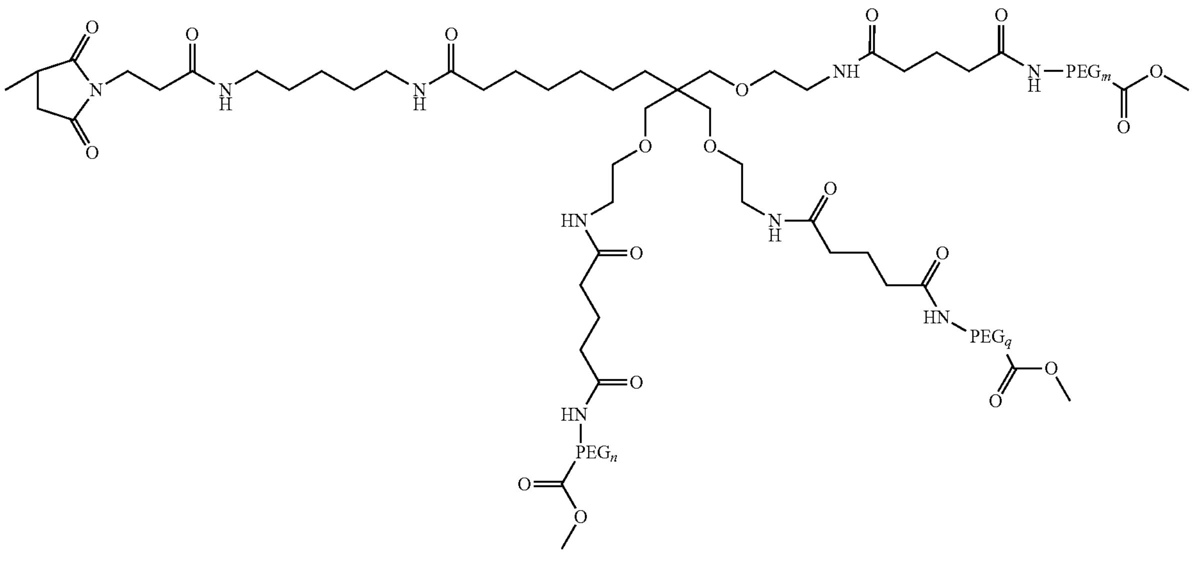

[In the formula, PEG is a polyethylene glycol chain, and each of n, m, and q is the number of ethylene glycol units and independently represents an integer of 5 to 100].

The linker of formula III is generally linked to the antibody at the terminus having the succinimidyl group and to the antitumor parts at the other multiple termini. The branched linker can be prepared, for example, as described in Reference Example 1 of PTL 7.

Technologies for bonding an antibody to an antitumor part through a linker are known in this technical field. For example, the bond between the antibody and the linker is a covalent bond or a non-covalent bond (an ionic bond, hydrophobic bonding, or the like), and is preferably a covalent bond. The bond is preferably such that when the conjugate of the present invention is administered to a subject, the antitumor part is not readily liberated in the blood. Such bonds include a bond between a maleimide group and a thiol group, a bond obtained by a reaction between a halo ester and a thiol, an amide bond between a carboxyl group and an amino group, a disulfide bond between a thiol group and another thiol group, a Schiff base from an amino group and an aldehyde group, a thioester bond between a thiol group and a carboxylic acid, an ester bond between a hydroxyl group and a carboxyl group, a bonding based on an amino group and a squaric acid derivative (for example, dimethyl squarate), a bond between a dienyl aldehyde group and an amino group, and the like. Specific examples of these bonds include a bond between a maleimide group present at one end of a linker and a thiol group contained in a cysteine residue on the antibody, a bond formed by dehydrative substitution between a succinimide group present at one end of a linker and an amino group contained in a lysine residue on an antibody (for example, WO2008/096760), a bond formed by dehydration condensation between an amino group present at one end of a linker and a carboxylic acid contained in aspartic acid or glutamic acid on an antibody (for example, WSCDI is used), and the like. For specific methods for bonding an antibody to a linker, see, for example, WO/2010/055950.

Meanwhile, the bond between the antitumor part and the antibody or the linker is a covalent bond or a non-covalent bond (an ionic bond, hydrophobic bonding, or the like), and is preferably a covalent bond. Especially when an antitumor compound is used as the antitumor part, the bond is preferably such that, when the conjugate of the present invention is administered to a subject, the antitumor part is not readily liberated in the blood. From such a viewpoint, the bond between the antitumor part and the antibody or the linker is preferably, but is not limited to, an ester bond, a carbamate bond, a carbonate bond, or a thiocarbamate bond, and more preferably an ester bond. When the bond is an ester bond, it can be expected that the bond is hydrolyzed with a carboxylesterase in a tumor tissue or non-enzymatically, so that the antitumor part is liberated from the conjugate of the present invention in a sustained release manner. When the bond is a carbamate bond, it can be expected that the antibody conjugate, as it is, is taken into cells by endocytosis, and then cleaved with a carboxylesterase in the cells, so that the antitumor part is liberated from the conjugate of the present invention in a sustained release manner. When the bond is a carbonate bond, it can be expected that the bond is hydrolyzed non-enzymatically, so that the antitumor part is liberated from the conjugate of the present invention in a sustained release manner. When the bond is a thiocarbamate bond, it can be expected that the bond is hydrolyzed non-enzymatically, so that the antitumor part is liberated from the conjugate of the present invention in a sustained release manner.

When an antitumor compound is used as the antitumor part in the conjugate of the present invention, the number of molecules of the antitumor compound conjugated per molecule of the antibody is not particularly limited theoretically, but is generally 1 to 10, and preferably 1 to 8, from the viewpoints of the stability of the conjugate, the ease of production, and the like.

For illustrative purposes, a case where SN-38 (10-hydroxy-7-ethyl-camptothecin) is used as the antitumor part and a polyethylene glycol linker is used as the linker is specifically described. However, even when a different combination is used, those skilled in the art can produce a targeted conjugate of the present invention by changing the reaction conditions, as appropriate.

(I) First, dehydration condensation of SN-38 and a polyethylene glycol having a carboxyl group at one end and having an amino group protected with Boc, Fmoc, or the like at the other end is conducted to introduce a polyethylene glycol linker to a hydroxyl group of SN-38.

(II) The product of (I) is mixed with a polyethylene glycol having a succinimide group at one end and a maleimide group at the other end to react the succinimide group with the amino group of the product of (I), so that the maleimide group is introduced to the polyethylene glycol linker.

(III) The product of (II) is mixed with an antibody to react the maleimide group in the product of (II) with a thiol group in the antibody. Thus, the product of (II) and the antibody are conjugated to each other to obtain the conjugate of the present invention.

The conjugate of the present invention can bind to insoluble fibrin in a tumor tissue and deliver the antitumor part to the tumor. In addition, the conjugate of the present invention has such an effect that it stays in the tumor tissue for a long period and continues to exhibit an antitumor effect for a long period. For this reason, the conjugate of the present invention can be used as an agent for preventing or treating a tumor. Specifically, by administering an effective amount of the conjugate of the present invention to a subject, a tumor in the mammal can be prevented or treated. Moreover, the conjugate of the present invention can exhibit the antitumor effect for a long period also by staying in a tumor tissue for a long period, and inhibiting the formation of blood vessels which provide nutrients to the tumor at a boundary region of the tumor.

Tumors to be treated or prevented in the present invention include, but are not limited to, solid cancer, for example, pancreatic cancer, gastric cancer, esophageal cancer, colorectal cancer, colon cancer, ovarian cancer, breast cancer, and pulmonary cancer.

The conjugate of the present invention is not targeted to cancer cells themselves, but is targeted to insoluble fibrin present at a site of leakage from a tumor blood vessel. The antibody of the present invention does not react with fibrinogen as described above, and has an extremely high affinity for insoluble fibrin. For this reason, the antibody-antitumor part conjugate having a high bioaffinity leaks selectively from tumor blood vessels owing to the EPR effect (enhanced permeation and retention effect) (because the conjugate is a polymer, the conjugate does not leak from normal blood vessels), binds to insoluble fibrin present in a tumor stroma after the leakage, and forms a foothold there. In other words, the conjugate of the present invention continues to be present at the fibrin in the stroma for a long period. For example, considering Example 6 described in PTL 7, when the antitumor part SN-38 is conjugated to the antibody of the present invention by an ester bond, SN-38 is liberated from the conjugate in a sustained release manner by a carboxylesterase in a tumor or spontaneously. Since SN-38 is a molecule having a low molecular weight, it is extremely highly possible that SN-38 will move about in the cancer tissue relatively freely, will be spread over the entire cancer, and will efficiently attack cancer cells. In addition, since the antitumor effect of SN-38 is time-dependent, such exposure of cancer cells to SN-38 for a long time can efficiently kill the cancer cells.

The agents of the present invention, including the above-described agent for visualizing a thrombus and the above-described agent for preventing or treating a tumor, may also comprise pharmaceutically acceptable carriers and additives in addition to the antibody. Examples of such carriers and additives include water, pharmaceutically acceptable organic solvents, collagen, polyvinyl alcohol, polyvinylpyrrolidone, carboxyvinyl polymer, sodium alginate, water-soluble dextran, carboxymethyl starch sodium salt, pectin, xanthan gum, gum arabic, casein, gelatin, agar, glycerin, propylene glycol, polyethylene glycol, Vaseline, paraffin, stearyl alcohol, stearic acid, mannitol, sorbitol, lactose, and the like. An additive used or a combinations of additives used are selected from the above-described ones, as appropriate, depending on the dosage form.

A method for administering the agent of the present invention is not particularly limited, and the agent of the present invention can be administered by oral administration or parenteral administration, for example, subcutaneous administration, intradermal administration, intramuscular administration, intravenous administration, transdermal administration, rectal administration, or nasal administration.

When the agent of the present invention is orally administered, the agent may be in the form of any one of tablets, capsules (hard capsules, soft capsules, microcapsules, and the like), granules, powders, pills, troches, oral aqueous solutions, liquids, suspensions, emulsions, syrups, and the like, or may be a dry product which is re-dissolved before use. Meanwhile, when the agent of the present invention is parenterally administered, it is possible to select a dosage form, for example, from injections (for example, solutions, emulsions, and suspensions) for intravenous injection (including infusion), intramuscular injection, intraperitoneal injection, and subcutaneous injection, external agents such as ointments (especially, ophthalmic ointments), creams, suppositories, cataplasms, ophthalmic solutions, collunariums, inhalants, liniments, and aerosols, and the like. When the agent of the present invention is in the form of an injection, the agent of the present invention is provided in the state of a unit dose ampoule or a multiple-dosage container.

These various pharmaceutical preparations can be produced in a usual manner, by selecting suitable ones from excipients, bulking agents, binders, wetting agents, disintegrators, lubricants, surfactants, dispersants, buffering agents, pH adjusting agents, preservatives, solubilizers, antiseptics, flavor modifiers, absorption enhancers, soothing agents, stabilizers, tonicity adjusting agents, and the like generally used for pharmaceuticals.

The antibody or the conjugate blended in the agent of the present invention may be, for example, 1 to 99% by weight and preferably 5 to 90% based on the total weight, although the amount varies depending on the type of the antibody, the types of the conjugate and the antitumor part contained in the conjugate, the application thereof, the dosage form, the administration route, and the like.

Moreover, the amount of the agent of the present invention administered and the intervals of the administration vary depending on the type of the antibody contained in the agent, the type of the antitumor part contained in the conjugate, the subject to which the agent is administered, the age and body weight of the subject, the administration route, and the number of times of administration, and can be changed over wide ranges.

The subject to which the agent of the present invention is administered is not particularly limited, and includes mammals, for example, human, domestic animals (cattle, pig, and the like), pet animals (dog, cat, and the like), experimental animals (mouse, rat, monkey, and the like). It is particularly preferable to use the agent of the present invention for a subject with a suspected thrombus-related disease or a subject with a thrombus-related disease. In addition, it is particularly preferable to use the agent comprising the conjugate of the present invention for a subject in which the presence of a tumor is suspected or for a subject having a tumor.

In the case of the agent for visualizing a thrombus, after the administration of the agent, the presence or the position of the antibody in a subject are visualized by using a label as an index. Preferably, the presence or the position of the antibody is visualized by a known imaging technology. As the imaging technology, computed tomography (CT), positron emission tomography (PET), nuclear magnetic resonance imaging (MRI), or other in vivo imaging systems can be used, although it varies depending on the label used, the type of the subject, the site to be imaged, and the like. This makes it possible to visualize the presence or the position of a thrombus in a subject on the basis of the label of the antibody.

EXAMPLES

Hereinafter, the present invention will be described more specifically on the basis of Examples and Reference Examples; however, the present invention is not limited to Examples below.

First, the pre sent inventors evaluated the properties and functions of the previously developed antibody which binds to fibrin and which does not bind to fibrinogen, namely, a chimeric antibody obtained from the antibody produced by the hybridoma 102-10 of Accession No. NITE P-923 (hereinafter, this antibody is also referred to as "102-10 antibody"), as described below. Note that, for the 102-10 antibody, see PTL 7 (Japanese Patent Application Publication No. 2012-72).

Reference Example 1

The fibrin specificity of the 102-10 antibody was analyzed by the method shown below.

<ELISA>

Each plate whose wells were coated with fibrinogen (fibrinogenplate) was prepared as follows. Specifically, fibrinogen from human or mouse (manufactured by Sigma, diluted with PBS) was added to a Maxi soap plate (manufactured by nunc) at 1 μg/100 μL/well, and the plate was sealed, and allowed to stand at 4° C. overnight.

Each fibrin plate was prepared as follows. Specifically, 100 μL of TBS containing 0.05 NIHU/mL thrombin (manufactured by Sigma), 1 mM $CaCl_2$, and 7 mM L-cysteine (manufactured by Merck) was added to the wells of the fibrinogen plate, which was then washed with TBS-T, and blocked with N102 (manufactured by NOF CORPORATION).

In addition, the 102-10 antibody was labeled with peroxidase by using Peroxidase Labeling Kit $NH_2$ (manufactured by DOJINDO). Further, the labeled 102-10 antibody was prepared at 1 μg/mL with Block Ace (manufactured by DS Pharma Biomedical Co., Ltd.).

Then, 100 μL of this diluted antibody solution was added to the fibrinogen plate and the fibrin plate, which were then shaken at room temperature for 30 minutes. After that, each plate was washed with TBS-T, and 100 μL of 1-Step Slow TMB (manufactured by Thermo) was added, and colorimetry was conducted. The stop reaction was conducted by adding 100 μL of 2 N $H_2SO_4$. In addition, the absorbance (O.D.) was obtained by measuring the absorption at an absorption wavelength of 450 nm with SPECTRA MAX190 (manufactured by Molecular Devices Japan KK). FIG. 1 shows the obtained results.

<Enzymatic Treatment of Insoluble Fibrin>

TBS containing 10 mg of fibrinogen, 0.02 M $CaCl_2$, 2.5 NIHU/mL thrombin, and 7 mM L-cysteine was incubated in a 1.5 mL tube at 37° C. for 1 hour to prepare fibrin clots.

The fibrin clots were degraded by adding, to the thus obtained fibrin clots,

2 μg/mL elastase (manufactured by Sigma),
70 μg/mL kallikrein (manufactured by Sigma),
10 μg/mL cathepsin B (manufactured by Sigma),
210 Units/mL cathepsin D (manufactured by Sigma),
200 ng/mL MMP-9 (manufactured by Sigma), or
0.1 μM plasmin (manufactured by American diagnostica).

Figure 2:
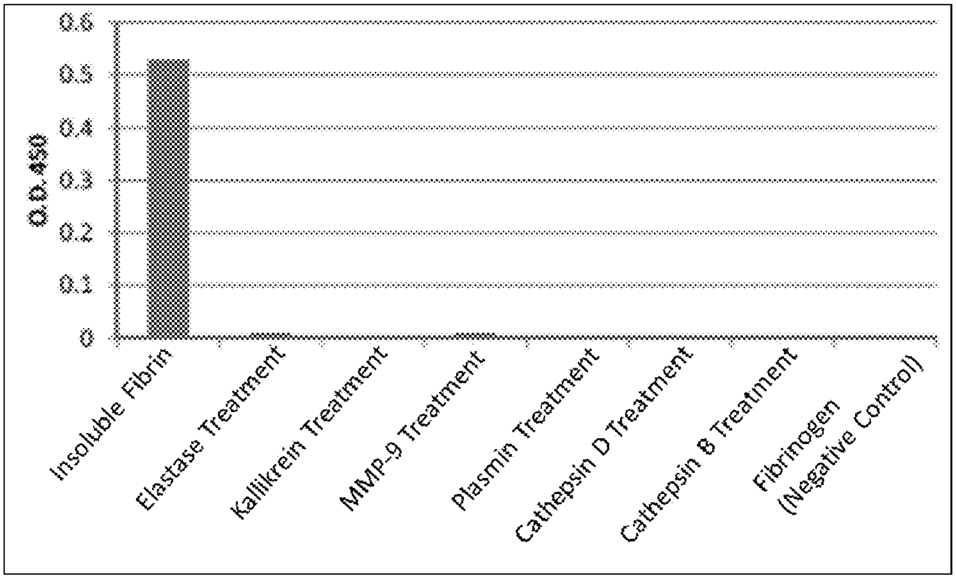
FIG. 2 is a graph showing the results obtained by analyzing the affinities of the 102-10 antibody for insoluble fibrin, products obtained by degrading insoluble fibrin with various enzymes (soluble fibrins), and fibrinogen by an ELISA method.

Then, each degradation product was coated onto an ELISA plate, and the reactivity of the labeled 102-10 antibody was analyzed. FIG. 2 shows the obtained results.

<Comparison with Commercially Available Antibodies>

The following two commercially available anti-fibrin antibodies were labeled with peroxidase:

NYB-T2G1 (manufactured by Accurate Chemical and Scientific), and

MH-1 (manufactured by American Tissue and Cell Culture).

Figure 3:
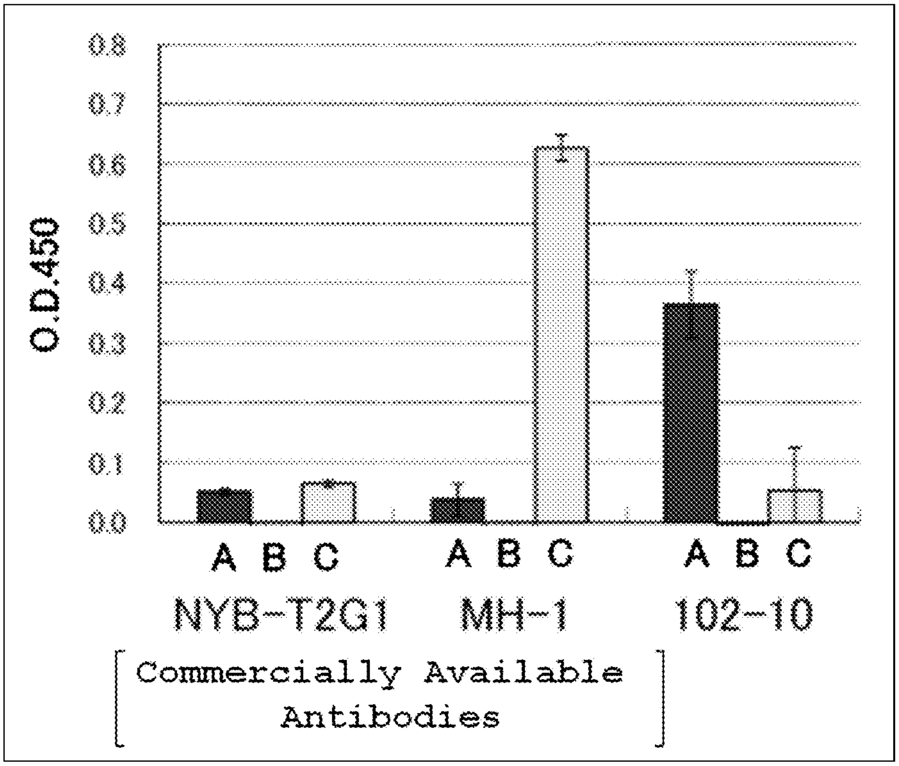
FIG. 3 is a graph showing the results obtained by analyzing the affinities of the 102-10 antibody and commercially available anti-fibrin antibodies (NYB-T2G1 and MH-1) for human insoluble fibrin, human fibrinogen, and D-dimer (a soluble fibrin) by an ELISA method. In the graph, each "A" indicates the affinity for human insoluble fibrin, each "B" indicates the affinity for human fibrinogen, and each "C" indicates the affinity for D-dimer.

Then, the affinities of these labeled antibodies and the above-described labeled 102-10 antibody were analyzed by using ELISA plates each coated with 1 μg of one of fibrin, fibrinogen, and D-dimer (manufactured by SEKISUI MEDICAL CO., LTD.). FIG. 3 shows the obtained results.

As is apparent from the results shown in FIG. 1, the 102-10 antibody exhibited high affinities for both human and mouse insoluble fibrin, but no affinity for fibrinogen was observed.

Moreover, as shown in FIG. 2, it has been shown that the 102-10 antibody binds to insoluble fibrin, but does not bind to the soluble fibrins (FDPs: fibrin degradation products) obtained by treating insoluble fibrin with various enzymes.

In addition, as shown in FIG. 3, NYB-T2G1 exhibited a low affinity for each of insoluble fibrin and D-dimer, because the epitope of NYB-T2G1 was covered after the fibrin polymerization. Meanwhile, MH-1 exhibited a high affinity for the soluble fibrin (D-dimer), but a low affinity for deposited fibrin (insoluble fibrin) as in the case of NYB-T2G1. On the other hand, the 102-10 antibody did not exhibit affinity for fibrinogen or D-dimer, and exhibited a high affinity only for deposited insoluble fibrin.

Reference Example 2

Immunostaining was conducted with the 102-10 antibody by the method shown below to try detection of the fibrin formation in tissue samples.

<Immunohistological Staining>

Figure 4:
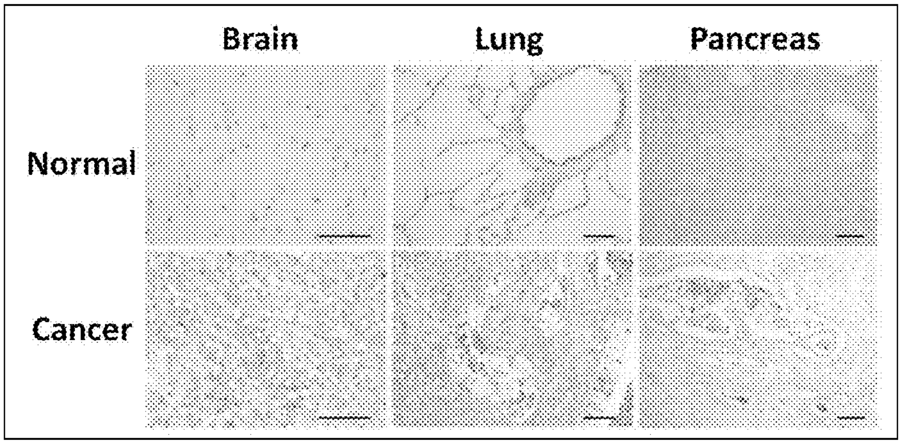
FIG. 4 shows micrographs showing the results of immunostaining of normal tissues and cancerous tissues of the brain, lung, and pancreas with the 102-10 antibody.
Figure 5:
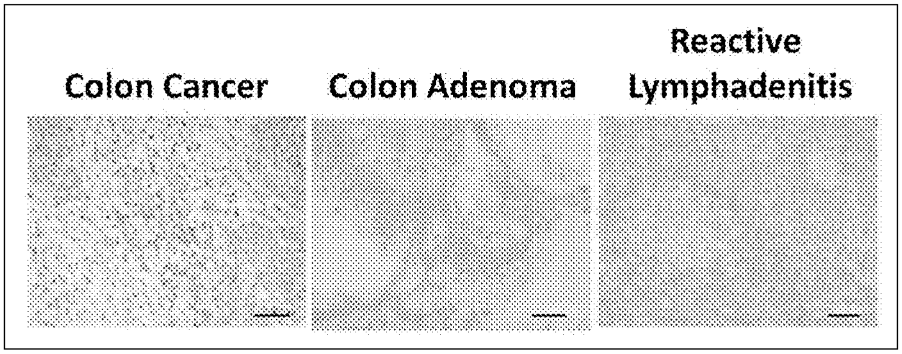
FIG. 5 shows micrographs showing the results of immunostaining of tissues of colon cancer, colon adenoma, and reactive lymphadenitis with the 102-10 antibody.
Figure 6:
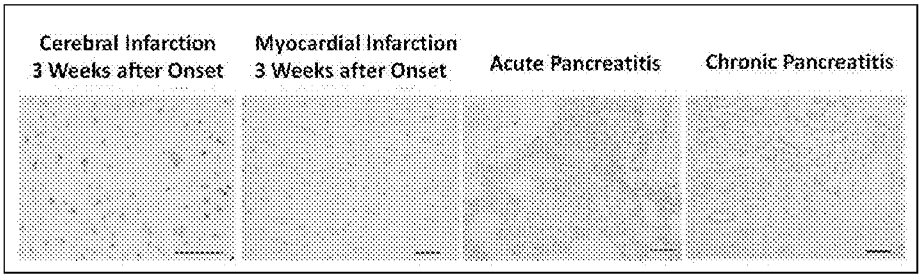
FIG. 6 shows micrographs showing the results of immunostaining of tissues with cerebral infarction (3 weeks had elapsed since the onset), myocardial infarction (3 weeks had elapsed since the onset), acute pancreatitis, and chronic pancreatitis with the 102-10 antibody.

Each paraffin-embedded tissue sample was subjected to a deparaffinization treatment, and antigen retrieval was conducted with 10 mM citrate buffer (pH 6) at 120° C. for 10 minutes. After a blocking treatment was conducted with 5% skimmed milk/PBS, the sample was incubated with 10 μg/mL of the 102-10 antibody at room temperature for 1 to 2 hours. Subsequently, the sample was incubated with a peroxidase-labeled anti-human IgG secondary antibody (manufactured by MBL) for 60 minutes. Then, after staining with DAB (manufactured by Dako), the nuclei were stained with haematoxylin (manufactured by MUTO PURE CHEMICALS CO., LTD.). FIGS. 4 to 6 show the obtained results.

As is apparent from the results shown in FIG. 4, fibrin formation was not detected with the 102-10 antibody in the normal tissues. In contrast, the formation of fibrin was detected with the 102-10 antibody in each of the cancerous brain tissue, lung tissue, and pancreas tissue. In addition, as shown in FIG. 5, fibrin was detected with the 102-10 antibody in colon cancer and colon adenoma as in the cases of the brain tumor, the pulmonary cancer, and the pancreatic cancer described above. However, fibrin formation was not observed in reactive lymphadenitis (lymphoma). As described above, it has been found that the 102-10 antibody can detect cancer specific fibrin formation (asymptomatic persistent formation of fibrin).

Moreover, although not shown in the drawings, fibrin was detected with the 102-10 antibody at the onset of each of cerebral infarction and myocardial infarction. On the other hand, as shown in FIG. 6, no fibrin formation was observed and disappearance of the fibrin was observed three weeks after the onset of each of the cerebral infarction and the myocardial infarction.

In addition, as shown in FIG. 6, fibrin was detected with the 102-10 antibody in acute pancreatitis, but such fibrin formation was not observed in chronic pancreatitis.

Reference Example 3

The fibrin detection performance of the 102-10 antibody was evaluated by the method shown below using disease model animals in which thrombi were formed.

<Animal Models>

A chemically-induced cancer model was prepared as follows. Specifically, a female FVB/N mouse was shaved, and DMBA diluted with acetone (250 μg/mL, manufactured by Sigma) was applied onto the mouse a single time, and one week later and every week after that, PMA diluted with acetone (25 μg/mL, manufactured by Sigma) was applied onto the mouse up to the 32nd week.

A cerebral infarction model was prepared as follows. Specifically, a female Sprague-Dawley rat was anesthetized with isoflurane (manufactured by Abbott). Then, the internal carotid artery was exposed, and cannulated with a polyethylene tube (with an inner diameter of 0.5 mm). In addition, in the middle cerebral artery, embolization was promoted with a 3-0 nylon filament (manufactured by Ethicon).

For preparation of an inflammation model, 2 mg of an anti-type II collagen antibody (manufactured by Chondrex) and an anti-type IV collagen antibody (Clone 35-4, established by the laboratory to which the present inventors belong) were intraperitoneally administered to a female DBA/1J mouse on Day 0. Further, 50 μg of LPS (manufactured by Chondrex) was intraperitoneally administered three days later.

A wound healing model was prepared as follows. Specifically, a female FVB/N mouse was anesthetized with isoflurane, and a 1 cm wound was created on the back of the mouse. Then, how the wound healed was observed every day, without treating the wound.

Figure 7:
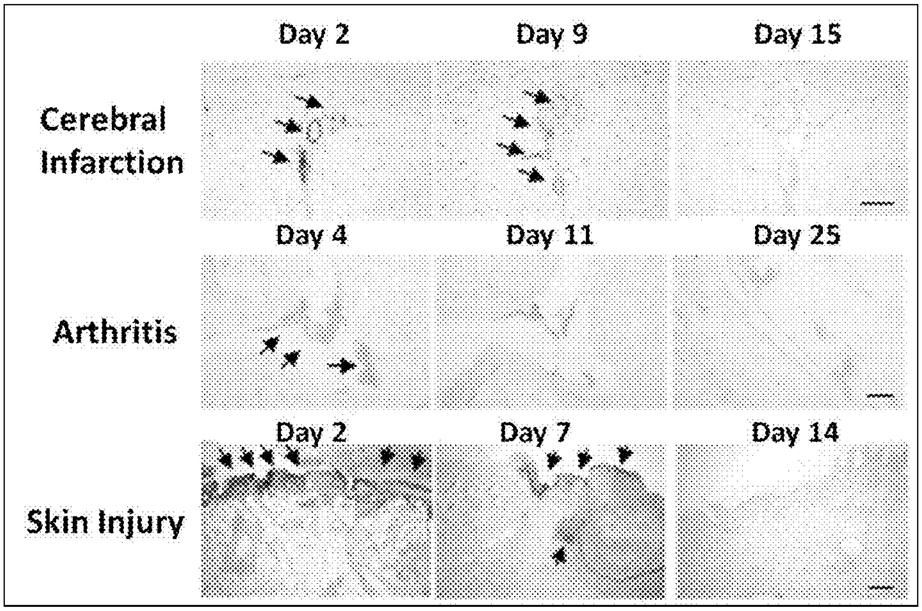
FIG. 7 shows micrographs showing the results of immunostaining of tissues with cerebral infarction, arthritis, and skin injury with the 102-10 antibody. Each day number in the figure represents the number of days elapsed from the onset or the wound creation. Meanwhile, each arrow indicates a site where insoluble fibrin (thrombus) is formed.

The above-described three model animals (the cerebral infarction model, the inflammation model, and the wound healing model) in which thrombus formation occurred were analyzed also by immunohistological staining using the 102-10 antibody. FIG. 7 shows the obtained results.

<Preparation of PET Probe>

Figure 8:
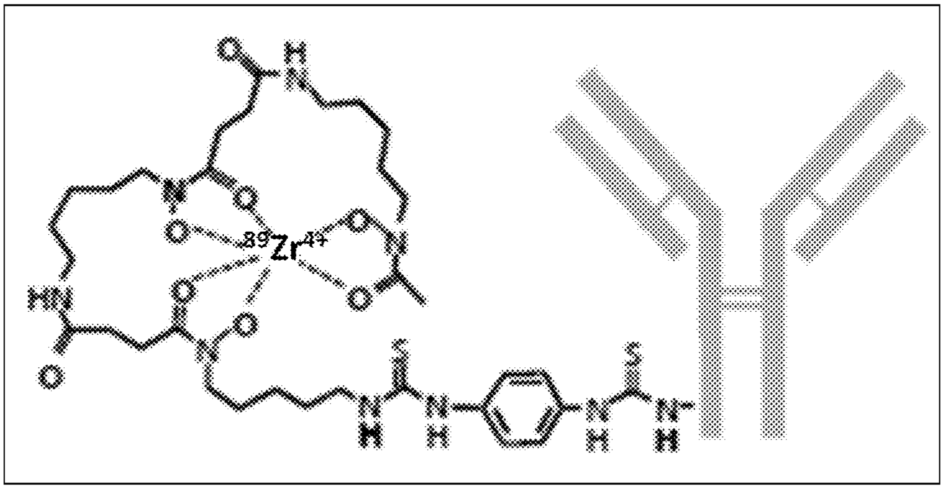
FIG. 8 shows a schematic diagram of a PET probe formed from the 102-10 antibody, p-isothiocyanatobenzyl-desferrioxamine B, and $^{89}$Zr nuclide.

The 102-10 antibody and p-isothiocyanatobenzyl-desferrioxamine B (DF, manufactured by Macrocyclics) were conjugated with a ratio of DF to the antibody being 1:1 to 1:3, and purified with Sephadex G-50 (GE). Meanwhile, $^{89}$Zr oxalate was prepared in a cyclotron. Then, the DF-conjugated 102-10 antibody (100 μg/20 μL PBS) and 5.0 to 5.6 MBq $^{89}$Zr-oxalate (3.7 to 5.6 GBq/mL, pH 7 to 9) were incubated for 1 hour at room temperature, followed by purification with Sephadex G-50. The thus obtained PET probe (see FIG. 8) achieved a radiochemical yield of 73 to 96%, had a purity of 96 to 98%, and achieved a specific activity of 37 to 44 kBq/μg which was measured by thin-layer chromatography using 50 mM DTPA.

<PET/CT>

Figure 9:
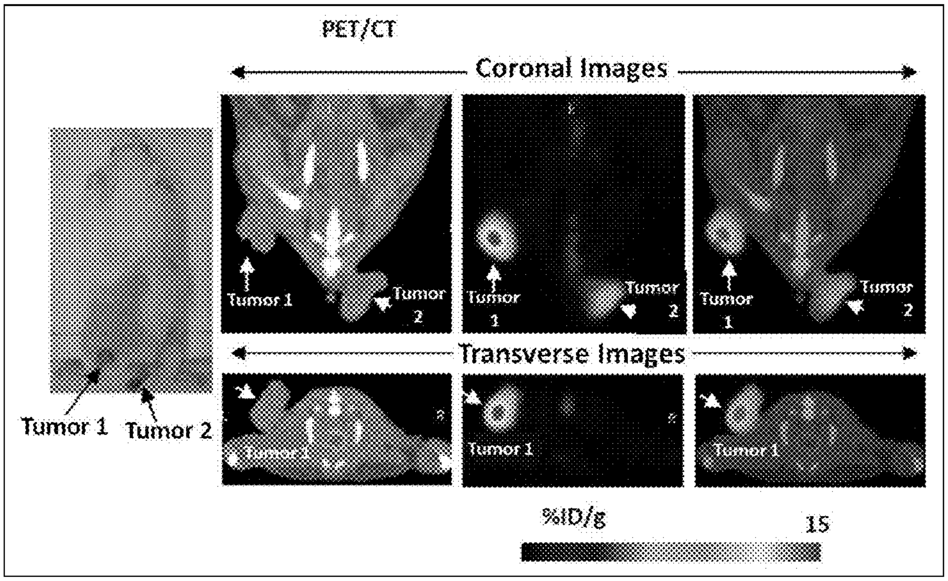
FIG. 9 shows photographs showing the results obtained by taking PET (positron emission tomography) and CT (computer tomography) images of a mouse with chemically induced cancer to which the PET probe shown in FIG. 8 was administered. In the drawing, a photograph of the appearance, CT images, PET images, and images obtained by overlapping the CT images with the PET images of the mouse with chemically induced cancer are shown in this order from the left.

The chemically-induced cancer model was subjected to PET/CT using the PET probe. Specifically, 3.7 MBq of the PET probe was administered to the chemically-induced cancer model mouse thorough the tail vein with the amount of the antibody administered being 100 μg/mouse in terms of the unlabeled antibody. The PET data were acquired by taking images using a small-animal PET system "Inveon" under anesthesia for 10 to 20 minutes. The body temperature was kept at 37° C. by using a lamp or a constant temperature pad. The images were processed by the 3D maximum a posteriori probability method (3D maximum a posteriori; 18 iterations with 16 subsets, β=0.2 resolution), without decay correction. After the PET scan, CT images were obtained with a small-animal PET system "R_mCT2" (manufactured by Rigaku Corporation) by using an X-ray light source at 90 kVp and 200 μA. FIG. 9 shows the obtained results.

Figure 10:
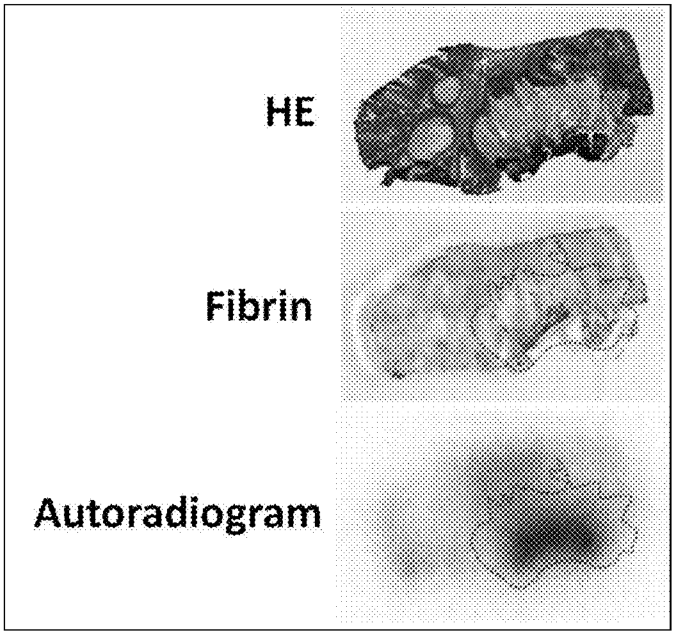
FIG. 10 shows photographs showing the results of observation of a cross section of a tumor isolated from the mouse with chemically induced cancer to which the PET probe shown in FIG. 8 was administered. In the drawing, "HE" indicates a result of observation of the cross section of the tumor after HE staining, "fibrin" indicates a result of observation of the cross section of the tumor after immunostaining with the 102-10 antibody, and "autoradiogram" indicates a result obtained by detecting radiation emitted from the PET probe at the cross section of the tumor.

In addition, after the X-ray photography, a tumor was taken out and embedded at −20° C. by using a frozen-tissue embedding agent (optimal-cutting-temperature (OCT) compound, Sakura Finetek Japan Co., Ltd.). A dry section with a 20-μm thickness was exposed to light using an imaging plate (manufactured by FUJIFILM Corporation), and stained (H & E staining) with haematoxylin and eosin (manufactured by MUTO PURE CHEMICALS CO., LTD.). In addition, the tumor taken out was analyzed also by immunostaining with the 102-10 antibody and by autoradiography using the antibody as a probe. FIG. 10 shows the obtained results.

As shown in FIG. 7, fibrin was detected with the 102-10 antibody at the onset or at the wound creation of each of the cerebral infarction, the arthritis, and the skin injury, but it was found that fibrin disappeared 2 to 3 weeks after the onset or the like in each of the disease models and the wound model, as in the cases of the analysis results of the cerebral infarction and myocardial infarction shown in FIG. 6.

In addition, as shown in FIGS. 9 and 10, it was found that the radioactively labeled 102-10 antibody was accumulated tumor-specifically in the body of the chemically-induced cancer model.

Accordingly, it has been shown that the 102-10 antibody can specifically detect fibrin not only in vitro but also in vivo. In addition, it has been also found that the 102-10 antibody can be utilized for detecting cancer in a living organism through such detection of fibrin. In addition, it has been also found that, in the case of a benign disease such as cerebral infarction, myocardial infarction, or inflammatory disease, a condition of the disease (progress information) can also be obtained through such detection of fibrin.

Reference Example 4

Detection of fibrin molecules in a fibrin clot with the 102-10 antibody was tried by the method shown below. In addition, the presence or absence of affinity of the 102-10 antibody for each of non-reduced fibrinogen and reduced fibrinogen was also analyzed.

<Immunofluorescent Staining of Human Fibrin Sections>

Figure 11:
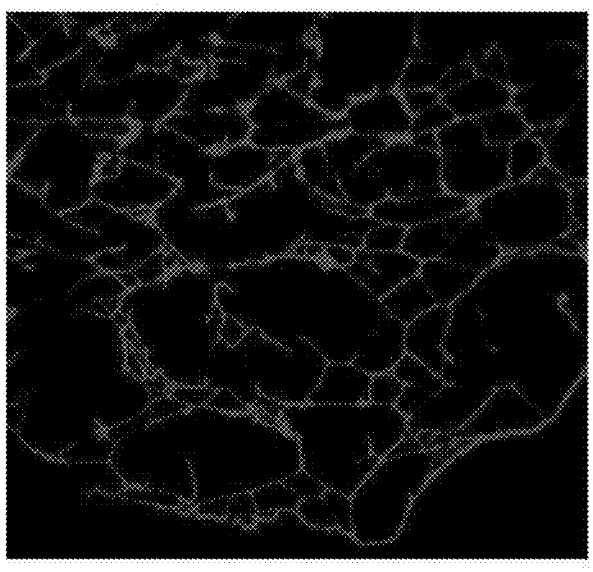
FIG. 11 is a micrograph showing the result of immunostaining of a fibrin clot with the 102-10 antibody.

Fibrin clots prepared by the same method as that described in Reference Example 1 were frozen by using the OCT compound to prepare frozen sections with a thickness of 6 μm. These frozen sections were air dried, then washed with PBS, and blocked with 5% skimmed milk/PBS. Subsequently, the 102-10 antibody labeled with Alexa Folur 647 protein labeling kit (manufactured by invitrogen) was added, followed by incubation for 1 hour. Then, the sections were sealed with Fluoromount G (manufactured by Southern Biotec). Then, the thus prepared samples were observed under a fluorescence microscope. FIG. 11 shows an obtained result.

<Western Blotting>

Figure 13:
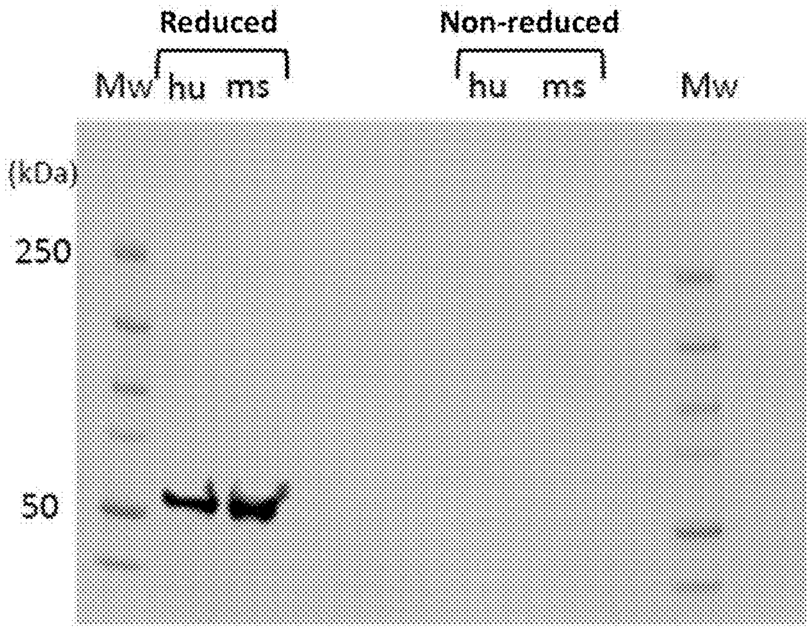
FIG. 13 is a photograph showing the results obtained by developing fibrinogen in a reduced state (the fibrinogen Aα chain, the fibrinogen Bβ chain, and the fibrinogen γ chain) and fibrinogen in a non-reduced state by SDS-PAGE followed by an analysis by Western blotting using the 102-10 antibody.

Fibrinogens (1 μg) from human and mouse were each diluted with each of a sample buffer containing 5% 2-mercaptoethanol (2-ME) (manufactured by Bio-Rad) and a sample buffer not containing 2-mercaptoethanol (manufactured by Bio-Rad). Then, only the samples diluted with the 2-ME-containing sample buffer were subjected to a heat treatment at 96° C. for 5 minutes. Subsequently, these samples were applied onto 4-20% TGX gel (manufactured by Bio-Rad), and electrophoresed with a constant voltage of 200 V for 30 minutes. The gel after the electrophoresis was transferred to Trans-Blot Turbo Mini PVDF (manufactured by Bio-Rad) under the conditions of 2.5 A, 25 V, and 7 minutes. The membrane after the transfer was transferred to SNAP i.d. (manufactured by Millipore), and blocked with 0.3% skimmed milk/0.1% PBS-T. Then, the membrane was incubated together with 1 μg/mL of a peroxidase-labeled 102-10 antibody to carry out the antigen-antibody reaction. Subsequently, after the membrane was washed with PBS-T, chemiluminescence was caused by ECL Prime (manufactured by GE) to detect the antigens to which the peroxidase-labeled 102-10 antibody was bound. FIG. 13 shows the obtained results.

Figure 12:
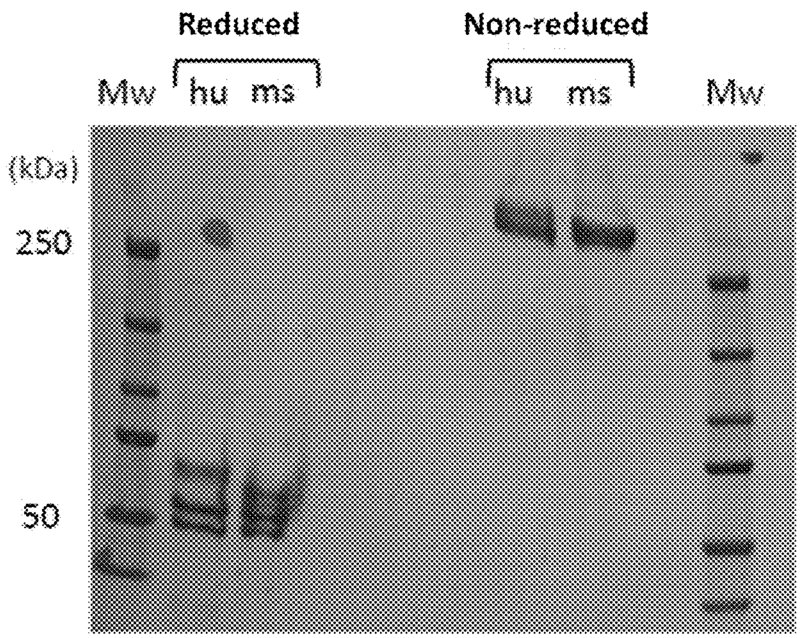
FIG. 12 is a photograph showing the results obtained by developing fibrinogen in a reduced state (the fibrinogen Aα chain, the fibrinogen Bβ chain, and the fibrinogen γ chain) and fibrinogen in a non-reduced state by SDS-PAGE, and staining the gels on which these proteins were developed with CBB. In the drawing, "hu" and "ms" respectively indicate that the developed fibrinogens were obtained from human and mouse. Each "Mw" indicates a lane in which molecular weight markers were developed (the same shall apply also in FIG. 13).

In addition, after this detection, the membrane was washed with PBS-T, and then stained with Coomassie Brilliant Blue (CBB). FIG. 12 shows the obtained results.

Note that the molecular weights of the three chains constituting fibrinogen are as follows. Specifically, the molecular weight of the Aα chain is approximately 67 KDa, the molecular weight of the Bβ chain is approximately 56 KDa, and the molecular weight of the γ chain is approximately 48 KDa.

As is apparent from the results shown in FIG. 11, a fibrin clot was stained like a mesh with the 102-10 antibody in reflection of the state where fibrin molecules were cross-linked in the fibrin clot.

In addition, as shown in FIGS. 12 and 13, the 102-10 antibody failed to detect fibrinogen in the non-reduced state as in the cases of the results shown in Reference Examples 1 to 3. In contrast, it has been shown that the 102-10 antibody can detect the Bβ chain (molecular weight: approximately 56 kDa) of fibrinogen in a reduced state where the formation of the complex is broken. Accordingly, it has been found that the epitope of the 102-10 antibody is present in a site in the fibrinogen Bβ chain exposed by denaturation (reduction).

Reference Example 5

Identification of the epitope of the 102-10 antibody was tried by the method shown below.

<Amino Acid Sequencing>

Fibrinogen reduced and heat-treated by the method described in Reference Example 4 was developed by SDS-PAGE. Subsequently, the fibrinogen Bβ chain was extracted from the gel by using EzStain Reverse and ATTOPREP MF (both manufactured by Atto). The extracted fibrinogen Bβ chain was cleaved with lysyl endopeptidase. Then, from the peptides cleaved from the fibrinogen Bβ chain, a peptide fragment which bound to the 102-10 antibody and which had the smallest molecular weight was extracted by Western blotting. Subsequently, this peptide fragment was subjected to amino acid sequencing.

Consequently, it has been found that the epitope of the 102-10 antibody is present in the region (86 amino acids) ranging from the histidine at position 179 to the lysine at position 264 of the fibrinogen Bβ chain (SEQ ID NO: 19) (see FIG. 14). Next, to narrow down the epitope of the 102-10 antibody, an experiment was conducted by the method shown below.

<Competitive Inhibition Experiment>

The above-described region composed of the 86 amino acids was further divided into five subsections to prepare synthetic peptides. A competitive inhibition experiment was conducted by using these peptides. Specifically, the synthetic peptides serially diluted from 0.01 to 100 μM were each added to 1 μg/mL of the 102-10 antibody, and incubated at room temperature for 30 minutes. To a fibrin plate, 100 μL of each of the mixture solutions of the antibody and the peptides was added, and incubated at room temperature for 30 minutes. After that, the plate was washed with TBS-T, and 100 μL of 1-Step Slow TMB (manufactured by Thermo) was added to perform colorimetry for 5 minutes. The stop reaction was conducted by adding 100 μL of 2 N $H_2SO_4$. In addition, the absorbance was obtained by measuring the absorbance at an absorption wavelength of 450 nm with SPECTRA MAX190 (manufactured by Molecular Devices Japan KK). FIG. 15 shows part of the obtained results. Note that the sequences of Fib-1, Fib-3, No. 1, and No. 5 shown in FIG. 15 are as follows.

Fib-1: NIPVVSGKECEEIIRKGGETS (Positions 179 to 252 of fibrinogen Bβ chain, SEQ ID NO: 21)

Fib-3: CNIPVVSGKE (Positions 231 to 240 of fibrinogen Bβ chain, SEQ ID NO: 22)

No. 1: HQLYIDETVNSNIPTNLRVLRSILENLRSK (Positions 179 to 208 of fibrinogen Bβ chain, SEQ ID NO: 23)

No. 5: CNIPVVSGKECEEIIR (Positions 231 to 246 of fibrinogen Bβ chain, SEQ ID NO: 1)

In addition, conjugates (Fib-1 KLH and Fib-3 KLH) of Fib-1 and Fib-3 to a carrier protein (KLH) were also prepared, and subjected to the competitive inhibition experiment.

As is apparent from the results shown in FIG. 15, in the region composed of the 86 amino acids (Positions 179 to 264 of the fibrinogen Bβ chain), the 102-10 antibody bound only to the site comprising the amino acids at positions 231 to 246 (No. 5), and did not bind to the site comprising the amino acids at positions 231 to 240 (Fib-3 KLH) included in the No. 5. Accordingly, it has been found that the epitope of the 102-10 antibody is the site comprising the amino acids at positions 231 to 246 of the fibrinogen Bβ chain (the amino acids shown in SEQ ID NO: 1).

In addition, fibrinogen is converted to a fibrin monomer in a case where the fibrinogen Bβ chain is cleaved between the arginine at position 44 and the glycine at the position 45 by thrombin to remove fibrinopeptide B (a polypeptide comprising the amino acids at positions 1 to 44 of the fibrinogen Bβ chain) or other cases. When the monomer is polymerized and cross-linked, insoluble fibrin is formed. Accordingly, the epitope of the 102-10 antibody in the insoluble fibrin is the site comprising the amino acids at positions 187 to 202 of the fibrinogen β chain (a protein obtained by removing fibrinopeptide B from the fibrinogen Bβ chain).

In addition, also when the fibrinogen Aβ chain is cleaved to remove fibrinopeptide A, while the fibrinogen Bβ chain is retained, another polymerizable fibrin monomer is formed from fibrinogen. Accordingly, the site comprising the amino acids at positions 231 to 246 of the fibrinogen Bβ chain can be an epitope of the 102-10 antibody also in insoluble fibrin.

Next, the identified epitope of the 102-10 antibody was analyzed by computer simulation. Consequently, it has been found that the epitope is a region which binds to the γ chain in the fibrinogen molecule (see FIG. 16, the arrow in the drawing points to the epitope of the 102-10 antibody). In addition, it has also been found that the site of the γ chain which binds to the Bβ chain is a region (KNWIQYKEGFGHLSP, SEQ ID NO: 2) ranging from the lysine at position 232 to the proline at position 246 of the fibrinogen γ chain (SEQ ID NO: 20).

Example 1

Preparation of Antibodies of Present Invention

From the results of the computer simulation shown in Reference Example 5, the 102-10 antibody cannot bind to fibrinogen, presumably because the epitope of the antibody is a region hidden in the molecule. In addition, fibrinogen is cleaved by thrombin to form fibrin monomers, and further the fibrin monomers are polymerized and cross-linked to be converted to insoluble fibrin. The 102-10 antibody can bind to insoluble fibrin, presumably because this structural change causes the exposure of the region hidden in the fibrinogen molecule.

In this respect, on the assumption that the site comprising the amino acids at positions 231 to 246 of the fibrinogen Bβ chain and the site comprising the amino acids at positions 232 to 246 of the fibrinogen γ chain is extremely useful for preparing an antibody which binds to insoluble fibrin but does not bind to fibrinogen, preparation of antibodies using each of these sites as an antigen was tried by the method shown below.

<Preparation of Antigens>

First, antigen genes encoding the site comprising the amino acids at positions 231 to 246 of the fibrinogen β chain or the site comprising the amino acids at positions 232 to 246 of the fibrinogen γ chain were each inserted into a restriction enzyme site (NdeI-HindIII) of pET21b. Thus, plasmid DNAs capable of expressing an antigenic peptide fused with a histidine tag were prepared. Then, each of these plasmid DNAs was introduced into *E. coli* BL21 (DE3) (manufactured by Novagen).

Next, the *E. coli* was inoculated into 200 mL of LB culture medium, and cultured at 37° C. and at 100 rpm. When the OD600 of the culture medium reached 0.6 to 0.8, the culturing was stopped temporarily, and the culture medium was allowed to stand for 15 minutes on ice. After that, IPTG (isopropyl-1-thio-β-D-galactopyranoside) was added at a final concentration of 1 mM to the culture medium, and then low-temperature culture was conducted at 18° C. and at 100 rpm. Then, after the addition of IPTG (expression induction of the antigen gene), the *E. coli* was cultured for 16 hours, and the cells were collected by centrifugation at 48,820 g for 15 minutes.

After the collection of the cells, the cells were suspended in 50 mM Tris-HCl (pH 8.5) containing 500 mM NaCl, and disrupted by sonication on ice. After the disruption, centrifugation was conducted at 48,820 g for 60 minutes, and the supernatant was recovered. Subsequently, the recovered supernatant was passed through 1 mL of Ni-NTA agarose (manufactured by Invitrogen) equilibrated with 50 mM Tris-HCl (pH 8.5) containing 500 mM NaCl. The agarose was washed with 50 mM Tris-HCl (pH 8.5) containing 5 mM imidazole and 500 mM NaCl. Then, an antigenic peptide trapped by the Ni-NTA agarose was eluted with PBS(−) containing 100 mM imidazole. The buffer of the obtained antigenic peptide was exchanged with PBS(−) by ultrafiltration using Amicon Ultra-15 10K (manufactured by Millipore). In addition, the purity of the purified antigenic peptide was checked by SDS-PAGE using SDS-page 10-20% (manufactured by DRC).

<Preparation of Antibodies>

Preparation of an antibody capable of binding to the site comprising the amino acids at positions 232 to 246 of the fibrinogen γ chain (hereinafter, also referred to as "anti-γ chain antibody") was outsourced to ITM CO., LTD. Specifically, the γ chain-derived antigenic peptide prepared as described above was intramuscularly injected into the tail base of a mouse. Then, a monoclonal antibody was prepared by using iliac lymph node of the mouse (see the mouse iliac lymph node method, Sado Y. et al., Acta Histochem. Cytochem., 2006, vol. 39, pp 89 to 94). An antibody capable of binding to the site comprising the amino acids at positions 231 to 246 of the fibrinogen Bβ chain (hereinafter, also referred to as "anti-β chain antibody") was prepared by the following method.

First, the histidine tag of the β chain-derived antigenic peptide prepared as described above was replaced with a 4M-tag in a usual manner. Then, the antigenic peptide fused with the 4M-tag (an immunogen) was administered to six mice. At the initial administration, an emulsion obtained by mixing FCA with the immunogen prepared at a concentration of the immunogen of 50 ug/mouse was intraperitoneally administered. Additional immunization was conducted every 2 to 3 weeks, for which 50 ug of the immunogen mixed with 200 uL of Sigma Adjuvant System was intraperitoneally administered to the mice.

At the third additional immunization and later, the blood was collected through the tail vein of the immunized mice 7 days after the administration. The blood was centrifuged at 12,000 r.p.m. for 10 minutes to separate serum components, which were stored frozen at −30° C. until measurement. Then, the antibody titers of the anti-fibrin antibodies contained in these serum components (immunized mice antiserums) were evaluated by an ELISA method using plates coated with the immunogen, fibrinogen, or fibrin, and the change of the antibody titers was examined.

Consequently, final immunization was conducted on a mouse in which the increase in antibody titer was observed, by administering 50 ug of the immunogen dissolved in PBS through the tail vein. Then, 4 days after the final immunization, the spleen was excised from the mouse, and splenic cells were obtained. All the obtained splenic cells were fused with p3.X63 mouse myeloma cells by the PEG method. The obtained fused cells were suspended in a culture medium for cell fusion, and seeded onto a 96-well plate at $2.0\times10^5$ cells/well in terms of splenic cells, and cultured.

The hybridoma culture supernatants obtained by the culturing were evaluated by an ELISA method using a plate coated with the immunogen to conduct a primary screening. Next, hybridomas determined to be positive in the primary screening were evaluated by an ELISA method using plates coated with the immunogen, fibrinogen, or fibrin to conduct secondary screening. Then, hybridomas determined to be positive in the secondary screening were selected as hybridomas which produced an antibody capable of binding to fibrin but incapable of binding to fibrinogen, and monoclonal hybridomas were obtained by the limiting dilution method.

Example 2

The anti-β chain antibodies and anti-γ chain antibodies prepared in Example 1 were compared with the 102-10 antibody by an ELISA method shown below. Note that, among hybridomas established in Example 1, Fib-0355 and Fib-03435 hybridomas were selected, and the antibodies produced by these hybridomas were subjected as anti-β chain antibodies to the ELISA method shown below. Meanwhile, among the hybridomas established in Example 1, 13-30 and 34-105 hybridomas were selected, and the antibodies produced by these hybridomas were subjected as anti-γ chain antibodies to the ELISA method shown below.

<ELISA Method>

Figure 16:
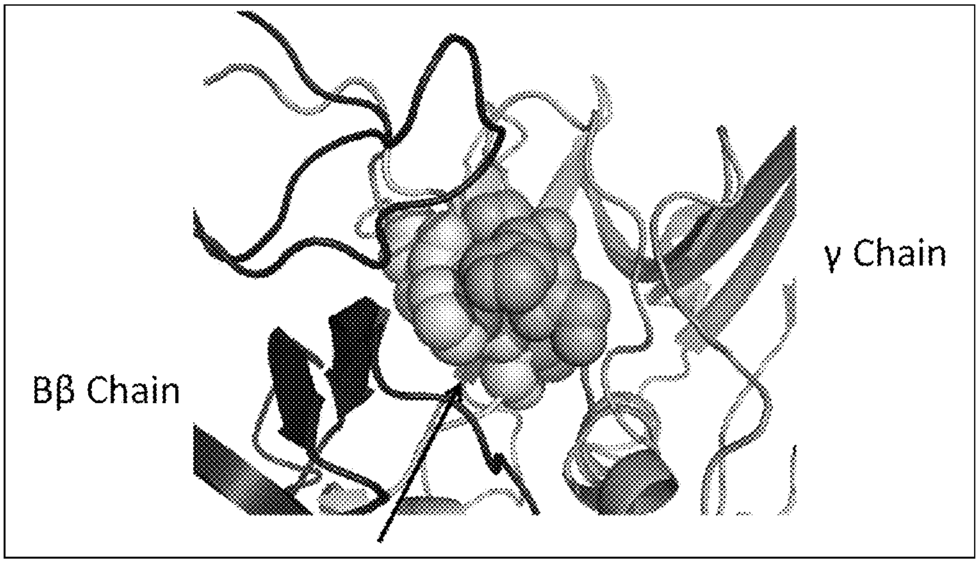
FIG. 16 is a diagram showing the result of a computer simulation analysis of the binding state of the fibrinogen Bβ chain and the fibrinogen γ chain in the fibrinogen molecule. In the diagram, the arrow indicates the epitope of the 102-10 antibody (the site comprising the amino acids at positions 231 to 246 of the fibrinogen Bβ chain).

Each of the antibody solutions (100 μL each) at 10 μg/mL was added to the fibrin plate and the fibrinogen plate, and allowed to stand at room temperature for 1 hour. After washing with TBS-T, Bethyl Anti-Human IgG-HRP (×1000 dilution) or Bethyl Anti-Mouse IgG-HRP (×10000 dilution) was added as a secondary antibody. Then, after washing with TBS-T, colorimetry was conducted with OPD for 10 minutes, and measurement was conducted at an absorption wavelength of 492 nm. FIG. 16 shows the obtained results.

Figure 17:
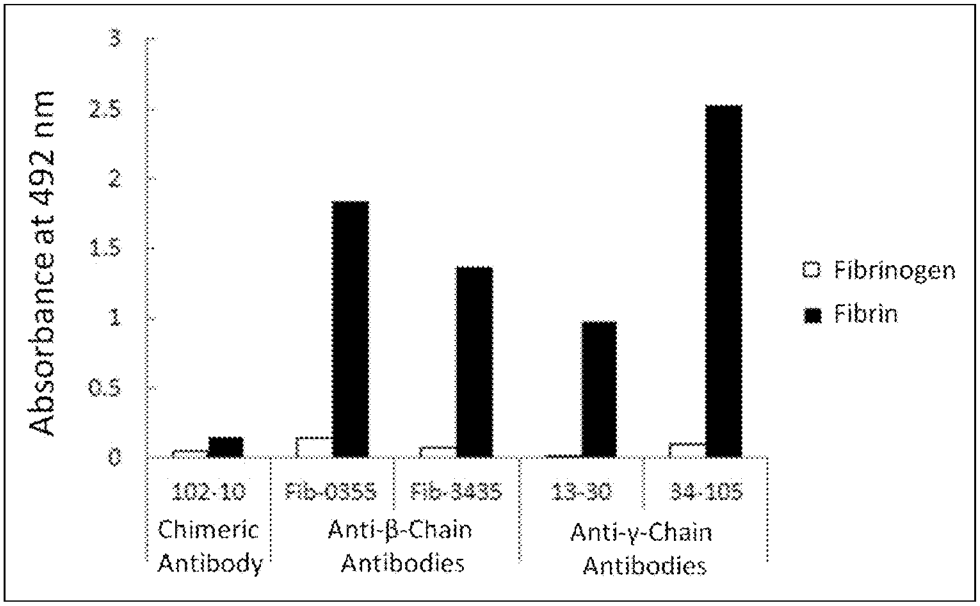
FIG. 17 is a graph showing the results obtained by analyzing the affinities of the 102-10 antibody, anti-β chain antibodies (Fib-0355 antibody and Fib-3435 antibody), and anti-γ chain antibodies (13-30 antibody and 34-105 antibody) for fibrin and fibrinogen by the ELISA method. Note that "Anti-β Chain Antibodies" indicates the results obtained by analyzing monoclonal antibodies obtained by immunizing mice with a polypeptide comprising the amino acids at positions 231 to 246 of the fibrinogen Bβ chain and "Anti-γ Chain Antibodies" indicates the results obtained by analyzing monoclonal antibodies obtained by immunizing mice with a polypeptide comprising the amino acids at positions 232 to 246 of the fibrinogen γ chain.

As is apparent from the results shown in FIG. 17, each of the currently prepared anti-β chain antibodies and anti-γ chain antibodies did not bind to fibrinogen and exhibited a high affinity for insoluble fibrin.

In addition, it was shown that the affinity for insoluble fibrin (the absorbance at 492 nm) of each of these antibodies was far higher than that of the 102-10 antibody. Specifically, the affinities of the Fib-0355 antibody, the Fib-3435 antibody, the 13-30 antibody, and the 34-105 antibody for insoluble fibrin were respectively 12 times, 9 times, 6 times, and 16 times that of the 102-10 antibody.

Moreover, the ratio of the affinity for insoluble fibrin to the affinity for fibrinogen (the absorbance at 492 nm) was 13 times for the Fib-0355 antibody, 18 times for the Fib-3435 antibody, 140 times for the 13-30 antibody, 25 times for the 34-105 antibody, and 3 times for the 102-10 antibody. Each of the currently prepared anti-β chain antibodies and anti-γ chain antibodies exhibited a higher specificity to insoluble fibrin than the 102-10 antibody.

Accordingly, the in vitro and in vivo detection of insoluble fibrin (thrombus), the diagnosis of a thrombus-related disease, the visualization of a thrombus (for example, PET/CT), and the like demonstrated in the above-described reference examples can, of course, be carried out also by using any of the anti-β chain antibodies and the anti-γ chain antibodies of the present invention. Moreover, the delivery of an antitumor compound or the like to a thrombus site disclosed by the present inventors in PTL 7 can, of course, be carried out also by using any of the anti-β chain antibodies and the anti-γ chain antibodies of the present invention.

Example 3

The sequences of the variable regions and the complementarity determining regions (CDR) of each of the antibody (Fib-0355 antibody) produced by the Fib-0355 and the antibody (34-105 antibody) produced by the 34-105 were determined by the method shown below.

First, total RNA was extracted from $1\times10^6$ cells of each hybridoma by using RNA iso Plus (manufactured by TAKARA) and RNeasy Mini Kit (manufactured by QIAGEN). cDNA was synthesized by a reverse transcription reaction using the extracted mRNA as a template and using High Capacity cDNA Reverse Transcription Kit (manufactured by Applied Biosystems) and the attached random primers. PCR was conducted by using the synthesized cDNA as a template and using a mixture of primers to clone the variable regions of the antibody. Note that the mixture of primers used was a mixture of 17 types of 5'-sense primer of kappa L chain variable region (Vκ), 3 types of 3'-reverse primer of Vκ, 19 types of 5'-sense primer of H chain variable region (VH), and 3 types of 3'-reverse primer of VH at a certain ratio. In addition, in this PCR, the polymerase used was platinum Taq DNA polymerase high fidelity (manufactured by Invitrogen), and the buffer solution and the like used were the attached reagents.

Next, the obtained PCR product was developed by agarose gel electrophoresis, and the bands which were assumed to correspond to the targeted VH and VL regions based on the sizes were cut out. Subsequently, cDNA was extracted from the gel by using QIAQuick Gel Extraction Kit (manufactured by Qiagen). The extracted cDNA was inserted into pGEM-T Easy Vector System (manufactured by promega) by the TA cloning, and multiple clones containing the target sequences were obtained. *E. coli* JM109 and DH5α were used as the hosts. The *E. coli* JM109 and DH5α were cultured respectively for approximately 12 hours and approximately 16 hours in LB culture media (containing 50 ug/ml ampicillin) for blue-white screen at 37° C., and then white colonies were selected. Then, plasmid DNA was extracted from the obtained white colonies by using QIAprep Spin Miniprep Kit (manufactured by QIAGEN).

Next, multiple clones containing antibody variable regions were subjected to sequencing by using BigDye Terminator v3.1 Cycle Sequencing Kit (manufactured by Applied Biosystems) and Applied Biosystems 3130xl Genetic Analyzer (manufactured by applied Biosystems/Hitachi) to obtain candidate sequences of the target antibody variable regions.

Then, the obtained candidate sequences were subjected to IgBLAST (http://www.ncbi.nlm.nih.gov/igblast/) of NCBI, and sorted into antibody sequences and myeloma-derived sequences. Moreover, the obtained sequence information of the variable regions were compared with the sequence information stored in the database (IMGT: http://www.imgt.org) on the web to determine the CDR regions. FIGS. 18 and 19 show the obtained results. In addition, the thus identified amino acid sequences of the variable regions and CDRs of the 34-105 antibody and the Fib-0355 antibody are also shown in Sequence Listing with SEQ ID NOs shown below.

The amino acid sequence of the L chain (light chain) variable region of the 34-105 antibody: SEQ ID NO: 3

The amino acid sequences of the L chain CDRs 1 to 3 of the 34-105 antibody: SEQ ID NOs: 4 to 6

The amino acid sequence of the H chain (heavy chain) variable region of the 34-105 antibody: SEQ ID NO: 7

The amino acid sequences of the H chain CDRs 1 to 3 of the 34-105 antibody: SEQ ID NOs: 8 to 10.

The amino acid sequence of the L chain (light chain) variable region of the Fib-0355 antibody: SEQ ID NO: 11

The amino acid sequences of the L chain CDRs 1 to 3 of the Fib-0355 antibody: SEQ ID NOs: 12 to 14

The amino acid sequence of the H chain (heavy chain) variable region of the Fib-0355 antibody: SEQ ID NO: 15

The amino acid sequences of the H chain CDRs 1 to 3 of the Fib-0355 antibody: SEQ ID NOs: 16 to 18.

INDUSTRIAL APPLICABILITY

As described above, according to the present invention, it is possible to provide an antibody which does not bind to fibrinogen and which has a high affinity for and a high specificity to insoluble fibrin. The use of such an antibody enables high-sensitive, reliable, and simple detection of the presence of insoluble fibrin and a thrombus, and, in turn, enables diagnosis of a thrombus-related disease. Moreover, the use of such an antibody enables a suitable compound or molecule to be delivered to a site where a thrombus is present, for example, to a tumor. Accordingly, the present invention is useful in the medical diagnosis field and the medicinal field.

SEQUENCE LISTING FREE TEXT

SEQ ID NO: 3
<223> light chain variable region (34-105)
SEQ ID NO: 4
<223> light chain CDR1 (34-105)
SEQ ID NO: 5
<223> light chain CDR2 (34-105)
SEQ ID NO: 6
<223> light chain CDR3 (34-105)
SEQ ID NO: 7
<223> heavy chain variable region (34-105)
SEQ ID NO: 8
<223> heavy chain CDR1 (34-105)
SEQ ID NO: 9
<223> heavy chain CDR2 (34-105)
SEQ ID NO: 10
<223> heavy chain CDR3 (34-105)
SEQ ID NO: 11
<223> light chain variable region (Fib-0355)
SEQ ID NO: 12
<223> light chain CDR1 (Fib-0355)
SEQ ID NO: 13
<223> light chain CDR2 (Fib-0355)
SEQ ID NO: 14
<223> light chain CDR3 (Fib-0355)
SEQ ID NO: 15
<223> heavy chain variable region (Fib-0355)
SEQ ID NO: 16
<223> heavy chain CDR1 (Fib-0355)
SEQ ID NO: 17
<223> heavy chain CDR2 (Fib-0355)
SEQ ID NO: 18
<223> heavy chain CDR3 (Fib-0355)

The invention claimed is:

1. An antibody which binds to insoluble fibrin and which does not bind to fibrinogen, wherein the antibody binds to a site shown in SEQ ID NO: 1 or a site shown in SEQ ID NO: 2.

2. The antibody according to claim 1, comprising:
- a light chain variable region comprising the amino acid sequences shown in SEQ ID NOs: 4 to 6; and
- a heavy chain variable region comprising the amino acid sequences shown in SEQ ID NOs: 8 to 10.

3. The antibody according to claim 1, comprising:
- a light chain variable region comprising the amino acid sequences shown in SEQ ID NOs: 12 to 14; and
- a heavy chain variable region comprising the amino acid sequences shown in SEQ ID NOs: 16 to 18.

4. The antibody according to claim 1, comprising:
- a light chain variable region comprising the amino acid sequence shown in SEQ ID NO: 3; and
- a heavy chain variable region comprising the amino acid sequence shown in SEQ ID NO: 7.

5. The antibody according to claim 1, comprising:
- a light chain variable region comprising the amino acid sequence shown in SEQ ID NO: 11; and
- a heavy chain variable region comprising the amino acid sequence shown in SEQ ID NO: 15.

6. A composition comprising the antibody according to claim 1 and a pharmaceutically acceptable carrier that allows for immunological measurement.

7. A composition comprising the antibody according to claim 1 and a pharmaceutically acceptable carrier that allows for diagnosing a disease characterized by the presence of a thrombus.

8. A composition comprising the antibody according to claim 1 and a pharmaceutically acceptable carrier that allows for visualizing a thrombus.

9. A method for detecting insoluble fibrin in a sample, comprising the steps of:
- (a) bringing the antibody according to claim 1 into contact with the sample; and
- (b) detecting whether or not the antibody is bound to insoluble fibrin in the sample.

10. A method for diagnosing a disease characterized by the presence of a thrombus in a subject, comprising the steps of:
- (a) bringing the antibody according to claim 1 into contact with a sample obtained from the subject; and
- (b) detecting whether or not the antibody is bound to insoluble fibrin in the sample.

11. A conjugate, comprising:
- the antibody according to claim 1; and
- an antitumor part.

12. A method for diagnosing a disease characterized by the presence of thrombus, comprising the steps of:
- administrating the antibody according to claim 1 labeled with a label to a subject;
- visualizing a position of a thrombus in the subject on the basis of the label of the antibody; and
- diagnosing whether the subject has developed the disease characterized by the presence of thrombus or has a risk of developing it at the visualized position.

* * * * *

SEQUENCE LISTING

<160> NUMBER OF SEQ ID NOS: 23

<210> SEQ ID NO 1
<211> LENGTH: 16
<212> TYPE: PRT
<213> ORGANISM: Homo sapiens

<400> SEQUENCE: 1

Cys Asn Ile Pro Val Val Ser Gly Lys Glu Cys Glu Glu Ile Ile Arg
1 5 10 15

<210> SEQ ID NO 2
<211> LENGTH: 15
<212> TYPE: PRT
<213> ORGANISM: Homo sapiens

<400> SEQUENCE: 2

Lys Asn Trp Ile Gln Tyr Lys Glu Gly Phe Gly His Leu Ser Pro
1 5 10 15

<210> SEQ ID NO 3
<211> LENGTH: 108
<212> TYPE: PRT
<213> ORGANISM: Mus musculus
<220> FEATURE:
<221> NAME/KEY: SITE
<222> LOCATION: (1)..(108)
<223> OTHER INFORMATION: Variable Region of Light Chain(34-105)

<400> SEQUENCE: 3

Asp Ile Val Ile Thr Gln Ser Pro Ala Ser Leu Ala Val Ser Leu Gly
1 5 10 15

Gln Arg Ala Thr Ile Ser Tyr Arg Ala Ser Lys Ser Val Ser Thr Ser
20 25 30

Gly Tyr Ser Tyr Met His Trp Asn Gln Gln Lys Pro Gly Gln Pro Pro
35 40 45

Arg Leu Leu Ile Tyr Leu Val Ser Asn Leu Glu Ser Gly Val Pro Ala
50 55 60

Arg Phe Ser Gly Ser Gly Ser Gly Thr Asp Phe Thr Leu Asn Ile His
65 70 75 80

Pro Val Glu Glu Glu Asp Ala Ala Thr Tyr Tyr Cys Gln His Ile Arg
85 90 95

Glu Leu Thr Arg Ser Glu Gly Gly Pro Ser Trp Lys
100 105

<210> SEQ ID NO 4
<211> LENGTH: 10
<212> TYPE: PRT
<213> ORGANISM: Mus musculus
<220> FEATURE:
<221> NAME/KEY: SITE
<222> LOCATION: (1)..(10)
<223> OTHER INFORMATION: CDR1 of Light Chain(34-105)

<400> SEQUENCE: 4

Lys Ser Val Ser Thr Ser Gly Tyr Ser Tyr
1 5 10

<210> SEQ ID NO 5
<211> LENGTH: 3
<212> TYPE: PRT
<213> ORGANISM: Mus musculus
<220> FEATURE:
<221> NAME/KEY: SITE
<222> LOCATION: (1)..(3)
<223> OTHER INFORMATION: CDR2 of Light Chain(34-105)

<400> SEQUENCE: 5

Leu Val Ser
1

<210> SEQ ID NO 6
<211> LENGTH: 8
<212> TYPE: PRT
<213> ORGANISM: Mus musculus
<220> FEATURE:
<221> NAME/KEY: SITE
<222> LOCATION: (1)..(8)
<223> OTHER INFORMATION: CDR3 of Light Chain(34-105)

<400> SEQUENCE: 6

Gln His Ile Arg Glu Leu Thr Arg
1 5

<210> SEQ ID NO 7
<211> LENGTH: 115
<212> TYPE: PRT
<213> ORGANISM: Mus musculus
<220> FEATURE:
<221> NAME/KEY: SITE
<222> LOCATION: (1)..(115)
<223> OTHER INFORMATION: Variable Region of Heavy Chain (34-105)

<400> SEQUENCE: 7

Glu Val Lys Leu Gln Glu Ser Gly Gly Gly Leu Val Lys Pro Gly Gly
1 5 10 15

Ser Leu Lys Leu Ser Cys Ala Ala Ser Gly Phe Thr Phe Ser Ser Tyr
20 25 30

Ala Met Ser Trp Val Arg Gln Thr Pro Glu Lys Arg Leu Glu Trp Val
35 40 45

Ala Ala Ile Ser Ser Gly Gly Thr Thr Tyr Tyr Pro Asp Ser Val Lys
50 55 60

Gly Arg Phe Thr Ile Ser Arg Asp Asn Ala Arg Asn Ile Leu Tyr Leu
65 70 75 80

Gln Met Ser Ser Leu Arg Ser Glu Asp Thr Ala Met Tyr Tyr Cys Val
85 90 95

Arg Gly Gly Thr Ile Gly Ala Tyr Trp Gly Gln Gly Thr Leu Val Thr
100 105 110

Val Ser Ala
115

<210> SEQ ID NO 8
<211> LENGTH: 8
<212> TYPE: PRT
<213> ORGANISM: Mus musculus
<220> FEATURE:
<221> NAME/KEY: SITE
<222> LOCATION: (1)..(8)
<223> OTHER INFORMATION: CDR1 of Heavy Chain(34-105)

<400> SEQUENCE: 8

Gly Phe Thr Phe Ser Ser Tyr Ala
1 5

<210> SEQ ID NO 9
<211> LENGTH: 7
<212> TYPE: PRT
<213> ORGANISM: Mus musculus

<220> FEATURE:
<221> NAME/KEY: SITE
<222> LOCATION: (1)..(7)
<223> OTHER INFORMATION: CDR2 of Heavy Chain(34-105)

<400> SEQUENCE: 9

```
Ile Ser Ser Gly Gly Thr Thr
1               5
```

<210> SEQ ID NO 10
<211> LENGTH: 9
<212> TYPE: PRT
<213> ORGANISM: Mus musculus
<220> FEATURE:
<221> NAME/KEY: SITE
<222> LOCATION: (1)..(9)
<223> OTHER INFORMATION: CDR3 of Heavy Chain(34-105)

<400> SEQUENCE: 10

```
Val Arg Gly Gly Thr Ile Gly Ala Tyr
1               5
```

<210> SEQ ID NO 11
<211> LENGTH: 98
<212> TYPE: PRT
<213> ORGANISM: Mus musculus
<220> FEATURE:
<221> NAME/KEY: SITE
<222> LOCATION: (1)..(98)
<223> OTHER INFORMATION: Variable Region of Light Chain(Fib-0355)

<400> SEQUENCE: 11

```
Pro Ser Ser Leu Ala Val Ser Ala Gly Glu Lys Val Thr Met Ser Cys
1               5                   10                  15

Lys Ser Ser Gln Ser Val Leu Tyr Ser Ser Asn Gln Lys Asn Tyr Leu
            20                  25                  30

Ala Trp Tyr Gln Gln Lys Pro Gly Gln Ser Pro Lys Leu Leu Ile Tyr
        35                  40                  45

Trp Ala Ser Thr Arg Glu Ser Gly Val Pro Asp Arg Phe Thr Gly Ser
    50                  55                  60

Gly Ser Gly Thr Asp Phe Thr Leu Thr Ile Ser Ser Val Gln Ala Glu
65                  70                  75                  80

Asp Leu Ala Val Tyr Tyr Cys Gln Gln Tyr Leu Ser Ser Tyr Thr Phe
                85                  90                  95

Gly Gly
```

<210> SEQ ID NO 12
<211> LENGTH: 10
<212> TYPE: PRT
<213> ORGANISM: Mus musculus
<220> FEATURE:
<221> NAME/KEY: SITE
<222> LOCATION: (1)..(10)
<223> OTHER INFORMATION: CDR1 of Light Chain(Fib-0355)

<400> SEQUENCE: 12

```
Gln Ser Val Leu Tyr Ser Ser Asn Gln Lys
1               5                   10
```

<210> SEQ ID NO 13
<211> LENGTH: 8
<212> TYPE: PRT
<213> ORGANISM: Mus musculus
<220> FEATURE:
<221> NAME/KEY: SITE
<222> LOCATION: (1)..(8)
<223> OTHER INFORMATION: CDR2 of Light Chain(Fib-0355)

<400> SEQUENCE: 13

Tyr Trp Ala Ser Thr Arg Glu Ser
1               5

<210> SEQ ID NO 14
<211> LENGTH: 4
<212> TYPE: PRT
<213> ORGANISM: Mus musculus
<220> FEATURE:
<221> NAME/KEY: SITE
<222> LOCATION: (1)..(4)
<223> OTHER INFORMATION: CDR3 of Light Chain(Fib-0355)

<400> SEQUENCE: 14

Tyr Leu Ser Ser
1

<210> SEQ ID NO 15
<211> LENGTH: 106
<212> TYPE: PRT
<213> ORGANISM: Mus musculus
<220> FEATURE:
<221> NAME/KEY: SITE
<222> LOCATION: (1)..(106)
<223> OTHER INFORMATION: Variable Region of Heavy Chain (Fib-0355)

<400> SEQUENCE: 15

Gly Pro Glu Leu Lys Lys Pro Gly Glu Thr Val Lys Ile Ser Cys Lys
1               5                   10                  15

Ala Ser Gly Tyr Thr Phe Thr Asn Tyr Gly Met Asn Trp Val Lys Gln
            20                  25                  30

Ala Pro Gly Lys Gly Leu Lys Trp Met Gly Trp Ile Asn Thr Asn Thr
        35                  40                  45

Gly Glu Pro Thr Tyr Ala Glu Glu Phe Lys Gly Arg Phe Ala Phe Ser
    50                  55                  60

Leu Glu Thr Ser Ala Ser Thr Ala Tyr Leu Gln Ile Asn Asn Leu Lys
65                  70                  75                  80

Asn Glu Asp Thr Ala Thr Tyr Phe Cys Ala Arg Leu Leu Asp Tyr Trp
                85                  90                  95

Gly Gln Gly Thr Thr Leu Thr Val Ser Ser
            100                 105

<210> SEQ ID NO 16
<211> LENGTH: 7
<212> TYPE: PRT
<213> ORGANISM: Mus musculus
<220> FEATURE:
<221> NAME/KEY: SITE
<222> LOCATION: (1)..(7)
<223> OTHER INFORMATION: CDR1 of Heavy Chain (Fib-0355)

<400> SEQUENCE: 16

Tyr Thr Phe Thr Asn Tyr Gly
1               5

<210> SEQ ID NO 17
<211> LENGTH: 6
<212> TYPE: PRT
<213> ORGANISM: Mus musculus
<220> FEATURE:
<221> NAME/KEY: SITE
<222> LOCATION: (1)..(6)

-continued

<223> OTHER INFORMATION: CDR2 of Heavy Chain (Fib-0355)

<400> SEQUENCE: 17

Asn Thr Asn Thr Gly Glu
1 5

<210> SEQ ID NO 18
<211> LENGTH: 5
<212> TYPE: PRT
<213> ORGANISM: Mus musculus
<220> FEATURE:
<221> NAME/KEY: SITE
<222> LOCATION: (1)..(5)
<223> OTHER INFORMATION: CDR3 of Heavy Chain (Fib-0355)

<400> SEQUENCE: 18

Arg Leu Leu Asp Tyr
1 5

<210> SEQ ID NO 19
<211> LENGTH: 491
<212> TYPE: PRT
<213> ORGANISM: Homo sapiens

<400> SEQUENCE: 19

Met Lys Arg Met Val Ser Trp Ser Phe His Lys Leu Lys Thr Met Lys
1 5 10 15

His Leu Leu Leu Leu Leu Leu Cys Val Phe Leu Val Lys Ser Gln Gly
20 25 30

Val Asn Asp Asn Glu Glu Gly Phe Phe Ser Ala Arg Gly His Arg Pro
35 40 45

Leu Asp Lys Lys Arg Glu Glu Ala Pro Ser Leu Arg Pro Ala Pro Pro
50 55 60

Pro Ile Ser Gly Gly Gly Tyr Arg Ala Arg Pro Ala Lys Ala Ala Ala
65 70 75 80

Thr Gln Lys Lys Val Glu Arg Lys Ala Pro Asp Ala Gly Gly Cys Leu
85 90 95

His Ala Asp Pro Asp Leu Gly Val Leu Cys Pro Thr Gly Cys Gln Leu
100 105 110

Gln Glu Ala Leu Leu Gln Gln Glu Arg Pro Ile Arg Asn Ser Val Asp
115 120 125

Glu Leu Asn Asn Asn Val Glu Ala Val Ser Gln Thr Ser Ser Ser Ser
130 135 140

Phe Gln Tyr Met Tyr Leu Leu Lys Asp Leu Trp Gln Lys Arg Gln Lys
145 150 155 160

Gln Val Lys Asp Asn Glu Asn Val Val Asn Glu Tyr Ser Ser Glu Leu
165 170 175

Glu Lys His Gln Leu Tyr Ile Asp Glu Thr Val Asn Ser Asn Ile Pro
180 185 190

Thr Asn Leu Arg Val Leu Arg Ser Ile Leu Glu Asn Leu Arg Ser Lys
195 200 205

Ile Gln Lys Leu Glu Ser Asp Val Ser Ala Gln Met Glu Tyr Cys Arg
210 215 220

Thr Pro Cys Thr Val Ser Cys Asn Ile Pro Val Val Ser Gly Lys Glu
225 230 235 240

Cys Glu Glu Ile Ile Arg Lys Gly Gly Glu Thr Ser Glu Met Tyr Leu
245 250 255

Ile Gln Pro Asp Ser Ser Val Lys Pro Tyr Arg Val Tyr Cys Asp Met

-continued

```
            260                 265                 270

Asn Thr Glu Asn Gly Gly Trp Thr Val Ile Gln Asn Arg Gln Asp Gly
        275                 280                 285

Ser Val Asp Phe Gly Arg Lys Trp Asp Pro Tyr Lys Gln Gly Phe Gly
    290                 295                 300

Asn Val Ala Thr Asn Thr Asp Gly Lys Asn Tyr Cys Gly Leu Pro Gly
305                 310                 315                 320

Glu Tyr Trp Leu Gly Asn Asp Lys Ile Ser Gln Leu Thr Arg Met Gly
                325                 330                 335

Pro Thr Glu Leu Leu Ile Glu Met Glu Asp Trp Lys Gly Asp Lys Val
            340                 345                 350

Lys Ala His Tyr Gly Gly Phe Thr Val Gln Asn Glu Ala Asn Lys Tyr
        355                 360                 365

Gln Ile Ser Val Asn Lys Tyr Arg Gly Thr Ala Gly Asn Ala Leu Met
    370                 375                 380

Asp Gly Ala Ser Gln Leu Met Gly Glu Asn Arg Thr Met Thr Ile His
385                 390                 395                 400

Asn Gly Met Phe Phe Ser Thr Tyr Asp Arg Asp Asn Asp Gly Trp Leu
                405                 410                 415

Thr Ser Asp Pro Arg Lys Gln Cys Ser Lys Glu Asp Gly Gly Gly Trp
            420                 425                 430

Trp Tyr Asn Arg Cys His Ala Ala Asn Pro Asn Gly Arg Tyr Tyr Trp
        435                 440                 445

Gly Gly Gln Tyr Thr Trp Asp Met Ala Lys His Gly Thr Asp Asp Gly
    450                 455                 460

Val Val Trp Met Asn Trp Lys Gly Ser Trp Tyr Ser Met Arg Lys Met
465                 470                 475                 480

Ser Met Lys Ile Arg Pro Phe Phe Pro Gln Gln
                485                 490


<210> SEQ ID NO 20
<211> LENGTH: 453
<212> TYPE: PRT
<213> ORGANISM: Homo sapiens

<400> SEQUENCE: 20

Met Ser Trp Ser Leu His Pro Arg Asn Leu Ile Leu Tyr Phe Tyr Ala
1               5                   10                  15

Leu Leu Phe Leu Ser Ser Thr Cys Val Ala Tyr Val Ala Thr Arg Asp
            20                  25                  30

Asn Cys Cys Ile Leu Asp Glu Arg Phe Gly Ser Tyr Cys Pro Thr Thr
        35                  40                  45

Cys Gly Ile Ala Asp Phe Leu Ser Thr Tyr Gln Thr Lys Val Asp Lys
    50                  55                  60

Asp Leu Gln Ser Leu Glu Asp Ile Leu His Gln Val Glu Asn Lys Thr
65                  70                  75                  80

Ser Glu Val Lys Gln Leu Ile Lys Ala Ile Gln Leu Thr Tyr Asn Pro
                85                  90                  95

Asp Glu Ser Ser Lys Pro Asn Met Ile Asp Ala Ala Thr Leu Lys Ser
            100                 105                 110

Arg Lys Met Leu Glu Glu Ile Met Lys Tyr Glu Ala Ser Ile Leu Thr
        115                 120                 125

His Asp Ser Ser Ile Arg Tyr Leu Gln Glu Ile Tyr Asn Ser Asn Asn
    130                 135                 140
```

-continued

```
Gln Lys Ile Val Asn Leu Lys Glu Lys Val Ala Gln Leu Glu Ala Gln
145                 150                 155                 160

Cys Gln Glu Pro Cys Lys Asp Thr Val Gln Ile His Asp Ile Thr Gly
                165                 170                 175

Lys Asp Cys Gln Asp Ile Ala Asn Lys Gly Ala Lys Gln Ser Gly Leu
            180                 185                 190

Tyr Phe Ile Lys Pro Leu Lys Ala Asn Gln Gln Phe Leu Val Tyr Cys
        195                 200                 205

Glu Ile Asp Gly Ser Gly Asn Gly Trp Thr Val Phe Gln Lys Arg Leu
    210                 215                 220

Asp Gly Ser Val Asp Phe Lys Lys Asn Trp Ile Gln Tyr Lys Glu Gly
225                 230                 235                 240

Phe Gly His Leu Ser Pro Thr Gly Thr Thr Glu Phe Trp Leu Gly Asn
                245                 250                 255

Glu Lys Ile His Leu Ile Ser Thr Gln Ser Ala Ile Pro Tyr Ala Leu
            260                 265                 270

Arg Val Glu Leu Glu Asp Trp Asn Gly Arg Thr Ser Thr Ala Asp Tyr
        275                 280                 285

Ala Met Phe Lys Val Gly Pro Glu Ala Asp Lys Tyr Arg Leu Thr Tyr
    290                 295                 300

Ala Tyr Phe Ala Gly Gly Asp Ala Gly Asp Ala Phe Asp Gly Phe Asp
305                 310                 315                 320

Phe Gly Asp Asp Pro Ser Asp Lys Phe Phe Thr Ser His Asn Gly Met
                325                 330                 335

Gln Phe Ser Thr Trp Asp Asn Asp Asn Asp Lys Phe Glu Gly Asn Cys
            340                 345                 350

Ala Glu Gln Asp Gly Ser Gly Trp Trp Met Asn Lys Cys His Ala Gly
        355                 360                 365

His Leu Asn Gly Val Tyr Tyr Gln Gly Gly Thr Tyr Ser Lys Ala Ser
    370                 375                 380

Thr Pro Asn Gly Tyr Asp Asn Gly Ile Ile Trp Ala Thr Trp Lys Thr
385                 390                 395                 400

Arg Trp Tyr Ser Met Lys Lys Thr Thr Met Lys Ile Ile Pro Phe Asn
                405                 410                 415

Arg Leu Thr Ile Gly Glu Gly Gln Gln His His Leu Gly Gly Ala Lys
            420                 425                 430

Gln Val Arg Pro Glu His Pro Ala Glu Thr Glu Tyr Asp Ser Leu Tyr
        435                 440                 445

Pro Glu Asp Asp Leu
    450


<210> SEQ ID NO 21
<211> LENGTH: 21
<212> TYPE: PRT
<213> ORGANISM: Homo sapiens

<400> SEQUENCE: 21

Asn Ile Pro Val Val Ser Gly Lys Glu Cys Glu Glu Ile Ile Arg Lys
1               5                   10                  15

Gly Gly Glu Thr Ser
            20


<210> SEQ ID NO 22
<211> LENGTH: 10
<212> TYPE: PRT
<213> ORGANISM: Homo sapiens
```

-continued

```
<400> SEQUENCE: 22

Cys Asn Ile Pro Val Val Ser Gly Lys Glu
1               5                   10


<210> SEQ ID NO 23
<211> LENGTH: 30
<212> TYPE: PRT
<213> ORGANISM: Homo sapiens

<400> SEQUENCE: 23

His Gln Leu Tyr Ile Asp Glu Thr Val Asn Ser Asn Ile Pro Thr Asn
1               5                   10                  15

Leu Arg Val Leu Arg Ser Ile Leu Glu Asn Leu Arg Ser Lys
            20                  25                  30
```